(12) United States Patent
Brown et al.

(10) Patent No.: US 7,290,450 B2
(45) Date of Patent: Nov. 6, 2007

(54) PROCESS DIAGNOSTICS

(75) Inventors: Gregory C. Brown, Chanhassen, MN (US); Marcos Peluso, Chanhassen, MN (US); Robert J. Karschnia, Chaska, MN (US)

(73) Assignee: Rosemount Inc., Eden Prairie, MN (US)

( * ) Notice: Subject to any disclaimer, the term of this patent is extended or adjusted under 35 U.S.C. 154(b) by 58 days.

(21) Appl. No.: 10/893,144

(22) Filed: Jul. 16, 2004

(65) Prior Publication Data

US 2005/0011278 A1    Jan. 20, 2005

Related U.S. Application Data

(60) Provisional application No. 60/488,613, filed on Jul. 18, 2003.

(51) Int. Cl.
*G01N 29/036* (2006.01)

(52) U.S. Cl. .................. 73/579; 73/597; 73/602; 73/861.23

(58) Field of Classification Search .............. 73/579, 73/592, 597, 602, 861.23, 861.22, 204.13, 73/861.42, 204.18
See application file for complete search history.

(56) References Cited

U.S. PATENT DOCUMENTS

| | | | |
|---|---|---|---|
| 3,096,434 A | 7/1963 | King .................... 235/151 |
| 3,404,264 A | 10/1968 | Kugler .................. 235/194 |
| 3,468,164 A | 9/1969 | Sutherland .............. 73/343 |
| 3,590,370 A | 6/1971 | Fleischer ................ 324/51 |
| 3,618,592 A | 11/1971 | Stewart ............... 128/2.05 R |
| 3,688,190 A | 8/1972 | Blum .................. 324/61 R |
| 3,691,842 A | 9/1972 | Akeley ................. 73/398 C |
| 3,701,280 A | 10/1972 | Stroman ................ 73/194 |
| 3,849,637 A | 11/1974 | Caruso et al. ........... 235/151 |
| 3,855,858 A | 12/1974 | Cushing ............... 73/194 EM |
| 3,948,098 A | 4/1976 | Richardson et al. ...... 73/861.24 |
| 3,952,759 A | 4/1976 | Ottenstein .............. 137/12 |
| 3,964,296 A | 6/1976 | Matzuk ............... 73/67.5 R |
| 3,973,184 A | 8/1976 | Raber .................. 324/51 |
| RE29,383 E | 9/1977 | Gallatin et al. .......... 137/14 |
| 4,058,975 A | 11/1977 | Gilbert et al. .......... 60/39.28 |

(Continued)

FOREIGN PATENT DOCUMENTS

CA    999950    11/1976

(Continued)

OTHER PUBLICATIONS

"A TCP\IP Tutorial" by, Socolofsky et al., Spider Systems Limited, Jan. 1991 pp. 1-23.

(Continued)

*Primary Examiner*—Hezron Williams
*Assistant Examiner*—Jacques M. Saint-Surin
(74) *Attorney, Agent, or Firm*—Westman, Champlin & Kelly, P.A.

(57) ABSTRACT

A diagnostic device for use in a industrial process includes monitoring electronics or diagnostic circuitry configured to diagnose or identify a condition or other occurrence in the industrial process. The system can be implemented in a process device such as a flowmeter, and in one example an acoustic flowmeter. A transducer can also be used and a frequency response, such as resonant frequency, can be observed.

18 Claims, 9 Drawing Sheets

U.S. PATENT DOCUMENTS

| | | | |
|---|---|---|---|
| 4,099,413 A | 7/1978 | Ohte et al. ................... 73/359 |
| 4,102,199 A | 7/1978 | Talpouras ................... 73/362 |
| 4,122,719 A | 10/1978 | Carlson et al. ............... 73/342 |
| 4,249,164 A | 2/1981 | Tivy ........................ 340/870.3 |
| 4,250,490 A | 2/1981 | Dahlke .................. 340/870.37 |
| 4,279,013 A | 7/1981 | Dahlke .................. 340/870.37 |
| 4,333,339 A | 6/1982 | McNeely et al. ............. 116/217 |
| 4,337,516 A | 6/1982 | Murphy et al. ............. 364/551 |
| 4,355,536 A | 10/1982 | McShane et al. ............. 73/633 |
| 4,393,711 A | 7/1983 | Lapides ....................... 73/592 |
| 4,399,824 A | 8/1983 | Davidson .................... 128/736 |
| 4,417,312 A | 11/1983 | Cronin et al. ............... 364/510 |
| 4,448,062 A | 5/1984 | Peterson et al. ................ 73/86 |
| 4,459,858 A | 7/1984 | Marsh ..................... 73/861.12 |
| 4,463,612 A | 8/1984 | Thompson ............... 73/861.22 |
| 4,517,468 A | 5/1985 | Kemper et al. ............... 290/52 |
| 4,528,869 A | 7/1985 | Kubo et al. ................... 74/695 |
| 4,530,234 A | 7/1985 | Cullick et al. .................. 73/53 |
| 4,540,468 A | 9/1985 | Genco et al. ................. 162/49 |
| 4,571,689 A | 2/1986 | Hildebrand et al. ......... 364/481 |
| 4,630,265 A | 12/1986 | Sexton ......................... 370/85 |
| 4,635,214 A | 1/1987 | Kasai et al. ................. 364/551 |
| 4,641,529 A | 2/1987 | Lorenzi et al. ............... 73/601 |
| 4,642,782 A | 2/1987 | Kemper et al. ............. 364/550 |
| 4,644,479 A | 2/1987 | Kemper et al. ............. 364/550 |
| 4,649,515 A | 3/1987 | Thompson et al. ......... 364/900 |
| 4,668,473 A | 5/1987 | Agarwal ....................... 422/62 |
| 4,686,638 A | 8/1987 | Furuse ........................ 364/558 |
| 4,707,796 A | 11/1987 | Calabro et al. .............. 364/552 |
| 4,720,806 A | 1/1988 | Schippers et al. ........... 364/551 |
| 4,736,367 A | 4/1988 | Wroblewski et al. ......... 370/85 |
| 4,736,763 A | 4/1988 | Britton et al. ................ 137/10 |
| 4,758,308 A | 7/1988 | Carr ........................... 162/263 |
| 4,777,585 A | 10/1988 | Kokawa et al. ............. 364/164 |
| 4,783,987 A | 11/1988 | Hager et al. .................... 73/32 |
| 4,807,151 A | 2/1989 | Citron ......................... 364/510 |
| 4,818,994 A | 4/1989 | Orth et al. ................... 340/501 |
| 4,831,564 A | 5/1989 | Suga ...................... 364/551.01 |
| 4,841,286 A | 6/1989 | Kummer ..................... 340/653 |
| 4,853,693 A | 8/1989 | Eaton-Williams ........... 340/588 |
| 4,873,655 A | 10/1989 | Kondraske .................. 364/553 |
| 4,898,022 A | 2/1990 | Yumoto et al. ................. 73/46 |
| 4,907,167 A | 3/1990 | Skeirik ........................ 364/500 |
| 4,924,418 A | 5/1990 | Bachman et al. ........... 364/550 |
| 4,926,364 A | 5/1990 | Brotherton .................. 364/581 |
| 4,934,196 A | 6/1990 | Romano ................... 73/861.38 |
| 4,939,753 A | 7/1990 | Olson ......................... 375/107 |
| 4,964,125 A | 10/1990 | Kim ......................... 371/15.1 |
| 4,988,990 A | 1/1991 | Warrior .................... 340/25.5 |
| 4,992,965 A | 2/1991 | Holter et al. ........... 364/551.01 |
| 5,005,142 A | 4/1991 | Lipchak et al. ............. 364/550 |
| 5,014,543 A | 5/1991 | Franklin et al. ......... 73/40.5 R |
| 5,019,760 A | 5/1991 | Chu et al. ................... 318/490 |
| 5,025,344 A | 6/1991 | Maly et al. ................... 361/88 |
| 5,043,862 A | 8/1991 | Takahashi et al. ........... 364/162 |
| 5,053,815 A | 10/1991 | Wendell ...................... 355/208 |
| 5,057,774 A | 10/1991 | Verhelst et al. .............. 324/537 |
| 5,067,099 A | 11/1991 | McCown et al. ............ 364/550 |
| 5,081,598 A | 1/1992 | Bellows et al. .............. 364/550 |
| 5,089,979 A | 2/1992 | McEachern et al. ... 364/571.04 |
| 5,089,984 A | 2/1992 | Struger et al. .............. 395/650 |
| 5,098,197 A | 3/1992 | Shepard et al. ............. 374/120 |
| 5,099,436 A | 3/1992 | McCown et al. ............ 364/550 |
| 5,103,409 A | 4/1992 | Shimizu et al. ............. 364/556 |
| 5,111,531 A | 5/1992 | Grayson et al. ............... 395/23 |
| 5,121,467 A | 6/1992 | Skeirik ......................... 395/11 |
| 5,122,794 A | 6/1992 | Warrior .................... 340/825.2 |
| 5,122,976 A | 6/1992 | Bellows et al. .............. 364/550 |
| 5,130,936 A | 7/1992 | Sheppard et al. ....... 364/551.01 |
| 5,134,574 A | 7/1992 | Beaverstock et al. .. 364/551.01 |
| 5,137,370 A | 8/1992 | McCullock et al. ......... 374/173 |
| 5,142,612 A | 8/1992 | Skeirik ......................... 395/11 |
| 5,143,452 A | 9/1992 | Maxedon et al. ............ 374/170 |
| 5,148,378 A | 9/1992 | Shibayama et al. .... 364/551.07 |
| 5,150,289 A | 9/1992 | Badavas ..................... 364/154 |
| 5,167,009 A | 11/1992 | Skeirik ......................... 395/27 |
| 5,175,678 A | 12/1992 | Frerichs et al. .............. 364/148 |
| 5,193,143 A | 3/1993 | Kaemmerer et al. .......... 395/51 |
| 5,197,114 A | 3/1993 | Skeirik ......................... 395/22 |
| 5,197,328 A | 3/1993 | Fitzgerald .................... 73/168 |
| 5,212,765 A | 5/1993 | Skeirik ......................... 395/11 |
| 5,214,582 A | 5/1993 | Gray ...................... 364/424.03 |
| 5,216,226 A | 6/1993 | Miyoshi ..................... 219/497 |
| 5,224,203 A | 6/1993 | Skeirik ......................... 395/22 |
| 5,228,780 A | 7/1993 | Shepard et al. ............. 374/175 |
| 5,235,527 A | 8/1993 | Ogawa et al. .......... 364/571.05 |
| 5,265,031 A | 11/1993 | Malczewski ................ 364/497 |
| 5,265,222 A | 11/1993 | Nishiya et al. ................. 395/3 |
| 5,269,311 A | 12/1993 | Kirchner et al. ............. 128/672 |
| 5,274,572 A | 12/1993 | O'Neill et al. .............. 364/550 |
| 5,282,131 A | 1/1994 | Rudd et al. .................. 364/164 |
| 5,282,261 A | 1/1994 | Skeirik ......................... 395/22 |
| 5,293,585 A | 3/1994 | Morita ......................... 395/52 |
| 5,303,181 A | 4/1994 | Stockton ...................... 365/96 |
| 5,305,230 A | 4/1994 | Matsumoto et al. ........ 364/495 |
| 5,311,421 A | 5/1994 | Nomura et al. ............. 364/157 |
| 5,317,520 A | 5/1994 | Castle ........................ 364/482 |
| 5,327,357 A | 7/1994 | Feinstein et al. ............ 364/502 |
| 5,333,240 A | 7/1994 | Matsumoto et al. .......... 395/23 |
| 5,340,271 A | 8/1994 | Freeman et al. ................ 415/1 |
| 5,347,843 A | 9/1994 | Orr et al. .......................... 73/3 |
| 5,349,541 A | 9/1994 | Alexandro, Jr. et al. .... 364/578 |
| 5,357,449 A | 10/1994 | Oh ......................... 364/551.01 |
| 5,361,628 A | 11/1994 | Marko et al. ................. 73/116 |
| 5,365,423 A | 11/1994 | Chand ........................ 364/140 |
| 5,365,787 A | 11/1994 | Hernandez et al. ........... 73/660 |
| 5,367,612 A | 11/1994 | Bozich et al. ................ 395/22 |
| 5,372,046 A * | 12/1994 | Kleven et al. ............ 73/861.22 |
| 5,384,699 A | 1/1995 | Levy et al. ............. 364/413.13 |
| 5,386,373 A | 1/1995 | Keeler et al. ............... 364/577 |
| 5,388,465 A | 2/1995 | Okaniwa et al. ......... 73/861.17 |
| 5,392,293 A | 2/1995 | Hsue .......................... 324/765 |
| 5,394,341 A | 2/1995 | Kepner .................. 364/551.01 |
| 5,394,543 A | 2/1995 | Hill et al. .................... 395/575 |
| 5,404,064 A | 4/1995 | Mermelstein et al. ....... 310/319 |
| 5,408,406 A | 4/1995 | Mathur et al. .............. 364/163 |
| 5,408,586 A | 4/1995 | Skeirik ......................... 395/23 |
| 5,410,495 A | 4/1995 | Ramamurthi .......... 364/511.05 |
| 5,414,645 A | 5/1995 | Hirano .................... 364/551.01 |
| 5,419,197 A | 5/1995 | Ogi et al. ..................... 73/659 |
| 5,429,001 A * | 7/1995 | Kleven .................... 73/861.22 |
| 5,430,642 A | 7/1995 | Nakajima et al. ............ 364/148 |
| 5,434,774 A | 7/1995 | Seberger .................... 364/172 |
| 5,436,705 A | 7/1995 | Raj ............................. 355/246 |
| 5,440,478 A | 8/1995 | Fisher et al. ................. 364/188 |
| 5,442,639 A | 8/1995 | Crowder et al. ............ 371/20.1 |
| 5,467,355 A | 11/1995 | Umeda et al. .......... 364/571.04 |
| 5,469,070 A | 11/1995 | Koluvek ..................... 324/713 |
| 5,469,156 A | 11/1995 | Kogura .................... 340/870.38 |
| 5,469,735 A | 11/1995 | Watanabe .................. 73/118.1 |
| 5,469,749 A | 11/1995 | Shimada et al. ......... 73/861.47 |
| 5,481,199 A | 1/1996 | Anderson et al. ........... 324/705 |
| 5,481,200 A | 1/1996 | Voegele et al. .............. 324/718 |
| 5,483,387 A | 1/1996 | Bauhahn et al. ............. 359/885 |
| 5,485,753 A | 1/1996 | Burns et al. ................. 73/720 |
| 5,486,996 A | 1/1996 | Samad et al. ............... 364/152 |
| 5,488,697 A | 1/1996 | Kaemmerer et al. .......... 395/51 |
| 5,489,831 A | 2/1996 | Harris ......................... 318/701 |
| 5,495,769 A | 3/1996 | Broden et al. ................. 73/718 |
| 5,497,661 A | 3/1996 | Stripf et al. .................. 73/611 |
| 5,509,311 A * | 4/1996 | Lew ............................. 73/661 |
| 5,510,779 A | 4/1996 | Maltby et al. ............ 340/870.3 |
| 5,511,004 A | 4/1996 | Dubost et al. .......... 364/551.01 |
| 5,519,330 A | 5/1996 | Yamauchi et al. ........... 324/700 |

| Patent | Date | Inventor | Class |
|---|---|---|---|
| 5,526,293 A | 6/1996 | Mozumder et al. | 364/578 |
| 5,539,638 A | 7/1996 | Keeler et al. | 364/424.03 |
| 5,548,528 A | 8/1996 | Keeler et al. | 364/497 |
| 5,555,190 A | 9/1996 | Derby et al. | 364/510 |
| 5,560,246 A | 10/1996 | Bottinger et al. | 73/361.04 |
| 5,561,599 A | 10/1996 | Lu | 364/164 |
| 5,570,034 A | 10/1996 | Needham et al. | 324/763 |
| 5,570,300 A | 10/1996 | Henry et al. | 364/551.01 |
| 5,571,944 A | 11/1996 | Pfeifer et al. | 73/24.04 |
| 5,572,420 A | 11/1996 | Lu | 364/153 |
| 5,573,032 A | 11/1996 | Lenz et al. | 137/486 |
| 5,591,922 A | 1/1997 | Segeral et al. | 73/861.04 |
| 5,594,180 A * | 1/1997 | Carpenter et al. | 73/861.356 |
| 5,598,521 A | 1/1997 | Kilgore et al. | 395/326 |
| 5,600,148 A | 2/1997 | Cole et al. | 250/495.1 |
| 5,608,650 A | 3/1997 | McClendon et al. | 364/510 |
| 5,623,605 A | 4/1997 | Keshav et al. | 395/200.17 |
| 5,629,870 A | 5/1997 | Farag et al. | 364/551.01 |
| 5,633,809 A | 5/1997 | Wissenbach et al. | 364/510 |
| 5,637,802 A | 6/1997 | Frick et al. | 73/724 |
| 5,640,491 A | 6/1997 | Bhat et al. | 395/22 |
| 5,650,943 A | 7/1997 | Powel et al. | 364/550 |
| 5,654,869 A | 8/1997 | Ohi et al. | 361/540 |
| 5,661,668 A | 8/1997 | Yemini et al. | 364/550 |
| 5,665,899 A | 9/1997 | Willcox | 73/1.63 |
| 5,669,713 A | 9/1997 | Schwartz et al. | 374/1 |
| 5,671,335 A | 9/1997 | Davis et al. | 395/23 |
| 5,672,247 A | 9/1997 | Pangalos et al. | 162/65 |
| 5,675,504 A | 10/1997 | Serodes et al. | 364/496 |
| 5,675,724 A | 10/1997 | Beal et al. | 395/182.02 |
| 5,680,109 A | 10/1997 | Lowe et al. | 340/608 |
| 5,682,317 A | 10/1997 | Keeler et al. | 364/431.03 |
| 5,700,090 A | 12/1997 | Eryurek | 374/210 |
| 5,703,575 A | 12/1997 | Kirpatrick | 340/870.17 |
| 5,704,011 A | 12/1997 | Hansen et al. | 395/22 |
| 5,705,754 A | 1/1998 | Keita et al. | 73/861.357 |
| 5,705,978 A | 1/1998 | Frick et al. | 340/511 |
| 5,708,211 A | 1/1998 | Jepson et al. | 73/861.04 |
| 5,708,585 A | 1/1998 | Kushion | 364/431.061 |
| 5,710,370 A | 1/1998 | Shanahan et al. | 73/1.35 |
| 5,710,708 A | 1/1998 | Wiegland | 364/470.1 |
| 5,713,668 A | 2/1998 | Lunghofer et al. | 374/179 |
| 5,719,378 A | 2/1998 | Jackson, Jr. et al. | 219/497 |
| 5,723,791 A | 3/1998 | Koch et al. | 73/597 |
| 5,736,649 A | 4/1998 | Kawasaki et al. | 73/861.23 |
| 5,741,074 A | 4/1998 | Wang et al. | 374/185 |
| 5,741,978 A * | 4/1998 | Gudmundsson | 73/861.04 |
| 5,742,845 A | 4/1998 | Wagner | 395/831 |
| 5,746,511 A | 5/1998 | Eryurek et al. | 374/2 |
| 5,747,701 A | 5/1998 | Marsh et al. | 73/861.23 |
| 5,752,008 A | 5/1998 | Bowling | 395/500 |
| 5,756,898 A | 5/1998 | Diatschenko et al. | 73/592 |
| 5,764,539 A | 6/1998 | Rani | 364/557 |
| 5,764,891 A | 6/1998 | Warrior | 395/200.2 |
| 5,781,024 A | 7/1998 | Blomberg et al. | 324/763 |
| 5,781,878 A | 7/1998 | Mizoguchi et al. | 701/109 |
| 5,790,413 A | 8/1998 | Bartusiak et al. | 364/485 |
| 5,801,689 A | 9/1998 | Huntsman | 345/329 |
| 5,805,442 A | 9/1998 | Crater et al. | 364/138 |
| 5,817,950 A | 10/1998 | Wiklund et al. | 73/861.66 |
| 5,825,664 A | 10/1998 | Warrior et al. | 700/7 |
| 5,828,567 A | 10/1998 | Eryurek et al. | 700/79 |
| 5,829,876 A | 11/1998 | Schwartz et al. | 374/1 |
| 5,848,383 A | 12/1998 | Yunus | 702/102 |
| 5,854,993 A | 12/1998 | Crichnik | 702/54 |
| 5,859,964 A | 1/1999 | Wang et al. | 395/185.01 |
| 5,869,772 A | 2/1999 | Storer | 73/861.24 |
| 5,874,676 A | 2/1999 | Maki, Jr. | 73/579 |
| 5,876,122 A | 3/1999 | Eryurek | 374/183 |
| 5,880,376 A | 3/1999 | Sai et al. | 73/861.08 |
| 5,887,978 A | 3/1999 | Lunghofer et al. | 374/179 |
| 5,908,990 A | 6/1999 | Cummings | 73/861.22 |
| 5,909,280 A | 6/1999 | Zavracky | 356/352 |
| 5,923,557 A | 7/1999 | Eidson | 364/471.03 |
| 5,924,086 A | 7/1999 | Mathur et al. | 706/25 |
| 5,926,096 A * | 7/1999 | Mattar et al. | 340/606 |
| 5,926,778 A | 7/1999 | Poppel | 702/130 |
| 5,936,514 A | 8/1999 | Anderson et al. | 340/310.01 |
| 5,940,290 A | 8/1999 | Dixon | 364/138 |
| 5,956,663 A | 9/1999 | Eryurek et al. | 702/183 |
| 5,970,430 A | 10/1999 | Burns et al. | 702/122 |
| 5,992,436 A | 11/1999 | Hellman | 137/1 |
| 6,002,952 A | 12/1999 | Diab et al. | 600/310 |
| 6,014,612 A | 1/2000 | Larson et al. | 702/183 |
| 6,014,902 A | 1/2000 | Lewis et al. | 73/861.12 |
| 6,016,523 A | 1/2000 | Zimmerman et al. | 710/63 |
| 6,016,706 A | 1/2000 | Yamamoto et al. | 9/6 |
| 6,017,143 A | 1/2000 | Eryurek et al. | 700/51 |
| 6,023,399 A | 2/2000 | Kogure | 361/23 |
| 6,026,352 A | 2/2000 | Burns et al. | 702/182 |
| 6,038,579 A | 3/2000 | Sekine | 708/400 |
| 6,045,260 A | 4/2000 | Schwartz et al. | 374/183 |
| 6,046,642 A | 4/2000 | Brayton et al. | 330/296 |
| 6,047,220 A | 4/2000 | Eryurek et al. | 700/28 |
| 6,047,222 A | 4/2000 | Burns et al. | 700/79 |
| 6,047,602 A | 4/2000 | Lynnworth | 73/632 |
| 6,052,655 A | 4/2000 | Kobayashi et al. | 702/184 |
| 6,061,603 A | 5/2000 | Papadopoulos et al. | 700/83 |
| 6,072,150 A | 6/2000 | Sheffer | 219/121.83 |
| 6,094,600 A | 7/2000 | Sharpe, Jr. et al. | 700/19 |
| 6,112,131 A | 8/2000 | Ghorashi et al. | 700/142 |
| 6,119,047 A | 9/2000 | Eryurek et al. | 700/28 |
| 6,119,529 A | 9/2000 | Di Marco et al. | 73/861.68 |
| 6,139,180 A | 10/2000 | Usher et al. | 374/1 |
| 6,145,529 A | 11/2000 | Hellman et al. | 137/1 |
| 6,147,756 A | 11/2000 | Zavracky et al. | 356/352 |
| 6,151,560 A | 11/2000 | Jones | 702/58 |
| 6,179,964 B1 | 1/2001 | Begemann et al. | 162/198 |
| 6,182,501 B1 | 2/2001 | Furuse et al. | 73/49.2 |
| 6,192,281 B1 | 2/2001 | Brown et al. | 700/2 |
| 6,195,591 B1 | 2/2001 | Nixon et al. | 700/2 |
| 6,199,018 B1 | 3/2001 | Quist et al. | 702/34 |
| 6,209,048 B1 | 3/2001 | Wolff | 710/62 |
| 6,236,948 B1 | 5/2001 | Eck et al. | 702/45 |
| 6,250,160 B1 | 6/2001 | Koch et al. | 73/602 |
| 6,263,487 B1 | 7/2001 | Stripf et al. | 717/1 |
| 6,272,438 B1 | 8/2001 | Cunningham et al. | 702/56 |
| 6,279,593 B1 | 8/2001 | Sheppard | 137/1 |
| 6,282,962 B1 | 9/2001 | Koch et al. | 73/602 |
| 6,289,735 B1 | 9/2001 | Dister et al. | 73/579 |
| 6,298,377 B1 | 10/2001 | Hartikainen et al. | 709/223 |
| 6,307,483 B1 | 10/2001 | Westfield et al. | 340/870.11 |
| 6,311,136 B1 | 10/2001 | Henry et al. | 702/45 |
| 6,317,701 B1 | 11/2001 | Pyotsia et al. | 702/188 |
| 6,327,914 B1 | 12/2001 | Dutton | 73/861.356 |
| 6,332,112 B1 | 12/2001 | Shukunami et al. | 702/56 |
| 6,338,283 B1 | 1/2002 | Blazquez et al. | 73/865.8 |
| 6,347,252 B1 | 2/2002 | Behr et al. | 700/2 |
| 6,356,191 B1 | 3/2002 | Kirkpatrick et al. | 340/501 |
| 6,360,277 B1 | 3/2002 | Ruckley et al. | 9/250 |
| 6,367,328 B1 | 4/2002 | Gorman et al. | 73/592 |
| 6,370,448 B1 | 4/2002 | Eryurek | 700/282 |
| 6,377,859 B1 | 4/2002 | Brown et al. | 700/79 |
| 6,397,114 B1 | 5/2002 | Eryurek et al. | 700/32 |
| 6,405,099 B1 | 6/2002 | Nagai et al. | 700/159 |
| 6,425,038 B1 | 7/2002 | Sprecher | 710/269 |
| 6,434,504 B1 | 8/2002 | Eryurek et al. | 702/130 |
| 6,449,574 B1 | 9/2002 | Eryurek et al. | 702/99 |
| 6,473,656 B1 | 10/2002 | Langels et al. | 700/17 |
| 6,473,710 B1 | 10/2002 | Eryurek | 702/133 |
| 6,480,793 B1 | 11/2002 | Martin | 702/45 |
| 6,505,517 B1 | 1/2003 | Eryurek et al. | 73/861.08 |
| 6,519,546 B1 | 2/2003 | Eryurek et al. | 702/130 |
| 6,532,392 B1 | 3/2003 | Eryurek et al. | 700/54 |
| 6,539,267 B1 | 3/2003 | Eryurek et al. | 700/51 |
| 6,546,814 B1 | 4/2003 | Choe et al. | 73/862.08 |

| | | | | | | |
|---|---|---|---|---|---|---|
| 6,556,145 B1 | 4/2003 | Kirkpatrick et al. ... 340/870.17 | | EP | 0 972 982 A2 | 1/2000 |
| 6,584,847 B1 | 7/2003 | Hirose ............ 73/579 | | EP | 1 022 626 A2 | 7/2000 |
| 6,594,603 B1 | 7/2003 | Eryurek et al. ............ 702/104 | | EP | 1 280 026 A1 | 1/2003 |
| 6,601,005 B1* | 7/2003 | Eryurek et al. ............ 702/104 | | FR | 2 302 514 | 9/1976 |
| 6,606,573 B2 | 8/2003 | Wheeler ............ 702/56 | | FR | 2 334 827 | 7/1977 |
| 6,611,775 B1 | 8/2003 | Coursolle et al. ............ 702/65 | | GB | 928704 | 6/1963 |
| 6,615,149 B1 | 9/2003 | Wehrs ............ 702/76 | | GB | 1 534 280 | 11/1978 |
| 6,650,280 B2 | 11/2003 | Arndt et al. ............ 342/124 | | GB | 1 534 288 | 11/1978 |
| 6,654,697 B1 | 11/2003 | Eryurek et al. ............ 702/47 | | GB | 2 310 346 A | 8/1997 |
| 6,701,274 B1 | 3/2004 | Eryurek et al. ............ 702/140 | | GB | 2 342 453 A | 4/2000 |
| 6,782,762 B2* | 8/2004 | Cage ............ 73/861.355 | | GB | 2 347 232 A | 8/2000 |
| 6,912,918 B1 | 7/2005 | Lynnworth et al. ...... 73/861.26 | | JP | 58-129316 | 8/1983 |
| 7,043,969 B2* | 5/2006 | Matsiev et al. ............ 73/54.41 | | JP | 59-116811 | 7/1984 |
| 7,148,611 B1 | 12/2006 | Liu ............ 310/366 | | JP | 59-163520 | 9/1984 |
| 2001/0010174 A1 | 8/2001 | Matsiev et al. ............ 73/592 | | JP | 59-211196 | 11/1984 |
| 2002/0013629 A1 | 1/2002 | Nixon et al. | | JP | 59-211896 | 11/1984 |
| 2002/0016675 A1 | 2/2002 | Vail, III et al. ............ 702/2 | | JP | 60-000507 | 1/1985 |
| 2002/0032544 A1 | 3/2002 | Reid et al. ............ 702/183 | | JP | 60-76619 | 5/1985 |
| 2002/0078752 A1 | 6/2002 | Braunling et al. ............ 73/627 | | JP | 60-131495 | 7/1985 |
| 2002/0101373 A1 | 8/2002 | Arndt et al. ............ 342/124 | | JP | 60-174915 | 9/1985 |
| 2002/0121910 A1 | 9/2002 | Rome et al. ............ 324/718 | | JP | 62-30915 | 2/1987 |
| 2002/0145568 A1 | 10/2002 | Winter ............ 343/701 | | JP | 62-50901 | 9/1987 |
| 2002/0148644 A1 | 10/2002 | Schultz et al. ............ 175/39 | | JP | 64-01914 | 1/1989 |
| 2002/0178787 A1 | 12/2002 | Matsiev et al. ............ 73/24.01 | | JP | 64-72699 | 3/1989 |
| 2003/0033040 A1 | 2/2003 | Billings ............ 700/97 | | JP | 2-05105 | 1/1990 |
| 2003/0041653 A1 | 3/2003 | Matsiev et al. ............ 73/54.25 | | JP | 3-229124 | 10/1991 |
| 2003/0045962 A1 | 3/2003 | Eryurek et al. ............ 700/128 | | JP | 4-70906 | 3/1992 |
| 2003/0056607 A1 | 3/2003 | Aronstam ............ 73/865.8 | | JP | 5-122768 | 5/1993 |
| 2003/0083576 A1 | 5/2003 | Bazarov et al. ............ 600/437 | | JP | 6-95882 | 4/1994 |
| 2003/0115936 A1 | 6/2003 | Kasameyer et al. ....... 73/54.23 | | JP | 06242192 | 9/1994 |
| 2004/0012264 A1 | 1/2004 | Burger et al. ............ 307/64 | | JP | 06-248224 | 10/1994 |
| 2004/0025593 A1 | 2/2004 | Hashimoto et al. ........... 73/643 | | JP | 7-063586 | 3/1995 |
| 2004/0055391 A1 | 3/2004 | Douglas et al. ............ 73/779 | | JP | 07234988 | 9/1995 |
| 2004/0128034 A1 | 7/2004 | Lenker et al. ............ 700/282 | | JP | 8-054923 | 2/1996 |
| 2004/0249583 A1 | 12/2004 | Eryurek et al. ............ 702/47 | | JP | 8-102241 | 4/1996 |
| 2005/0011278 A1 | 1/2005 | Brown et al. ............ 73/861.18 | | JP | 8-136386 | 5/1996 |
| 2005/0145019 A1* | 7/2005 | Matsiev et al. ............ 73/53.01 | | JP | WO 08-114638 | 5/1996 |
| 2005/0189017 A1 | 9/2005 | Eryurek ............ 137/487.5 | | JP | 8-166309 | 6/1996 |
| 2006/0118647 A1 | 6/2006 | Cheskaty et al. ............ 236/93 | | JP | 8-247076 | 9/1996 |
| 2006/0118648 A1 | 6/2006 | Armstrong et al. ........... 236/93 | | JP | 8-313466 | 11/1996 |
| 2006/0122808 A1 | 6/2006 | Quake et al. ............ 702/183 | | JP | 2712625 | 10/1997 |
| | | | | JP | 2712701 | 10/1997 |
| FOREIGN PATENT DOCUMENTS | | | | JP | 2753592 | 3/1998 |
| | | | | JP | 07225530 | 5/1998 |
| DE | 32 13 866 A1 | 10/1983 | | JP | 10-232170 | 9/1998 |
| DE | 35 40 204 C1 | 9/1986 | | JP | 11-083575 | 3/1999 |
| DE | 3913715 A1 * | 11/1989 | | JP | 2003315254 A | 11/2003 |
| DE | 40 08 560 A1 | 9/1990 | | RU | 2 190 267 | 9/2002 |
| DE | 43 43 747 | 6/1994 | | WO | WO 94/25933 | 11/1994 |
| DE | 44 33 593 A1 | 6/1995 | | WO | WO 95/23361 | 8/1995 |
| DE | 195 02 499 A1 | 8/1996 | | WO | WO 96/11389 | 4/1996 |
| DE | 296 00 609 U1 | 3/1997 | | WO | WO 96/12993 | 5/1996 |
| DE | 197 04 694 A1 | 8/1997 | | WO | WO 96/39617 | 12/1996 |
| DE | 19930660 A1 | 7/1999 | | WO | WO 97/21157 | 6/1997 |
| DE | 199 05 071 | 8/2000 | | WO | WO 97/25603 | 7/1997 |
| DE | 19905071 A1 | 8/2000 | | WO | WO 98/06024 | 2/1998 |
| DE | 299 17 651 U1 | 12/2000 | | WO | WO 98/13677 | 4/1998 |
| DE | 100 36 971 A1 | 2/2002 | | WO | WO 98/14855 | 4/1998 |
| DE | 102 23 725 A1 | 4/2003 | | WO | WO 98/20469 | 5/1998 |
| EP | 0 122 622 A1 | 10/1984 | | WO | WO 98/39718 | 9/1998 |
| EP | 0 413 814 A1 | 2/1991 | | WO | WO 99/19782 | 4/1999 |
| EP | 0 487 419 A2 | 5/1992 | | WO | WO 00/41050 | 7/2000 |
| EP | 0 512 794 A2 | 11/1992 | | WO | WO 00/55700 | 9/2000 |
| EP | 0 594 227 A1 | 4/1994 | | WO | WO 00/70531 | 11/2000 |
| EP | 0 624 847 A1 | 11/1994 | | WO | WO 01/01213 A1 | 1/2001 |
| EP | 0 644 470 A2 | 3/1995 | | WO | WO 01/77766 | 10/2001 |
| EP | 0 697 586 A2 | 2/1996 | | WO | WO 02/27418 | 4/2002 |
| EP | 0 697 595 A1 | 2/1996 | | | | |
| EP | 0 825 506 A2 | 7/1997 | | | | |
| EP | 0 827 096 A2 | 9/1997 | | | | |
| EP | 0 838 768 A2 | 9/1997 | | | | |
| EP | 0 807 804 A2 | 11/1997 | | | | |
| EP | 1 058 093 A1 | 5/1999 | | | | |

OTHER PUBLICATIONS

"Approval Standards For Explosionproof Electrical Equipment General Requirements", Factory Mutual Research, Cl. No. 3615, Mar. 1989, pp. 1-34.

"Approval Standard Intrinsically Safe Apparatus and Associated Apparatus For Use In Class I, II, and III, Division 1 Hazardous (Classified) Locations", Factory Mutual Research, Cl. No. 3610, Oct. 1988, pp. 1-70.

"Automation On-line" by, Phillips et al., Plant Services, Jul. 1997, pp. 41-45.

"Climb to New Heights by Controlling your PLCs Over the Internet" by, Phillips et al., Intech, Aug. 1998, pp. 50-51.

"CompProcessor For Piezoresistive Sensors" MCA Technologies Inc. (MCA7707), pp. 1-8.

"Ethernet emerges as viable, inexpensive fieldbus", Paul G. Schreier, Personal Engineering, Dec. 1997, p. 23-29.

"Ethernet Rules Closed-loop System" by, Eidson et al., Intech, Jun. 1998, pp. 39-42.

"Fieldbus Standard for Use in Industrial Control Systems Part 2: Physical Layer Specification and Service Definition", ISA-S50, Feb. 1992, pp. 1-93.

"Fieldbus Standard for Use in Industrial Control Systems Part 3: Data Link Service Definition", ISA-S50. Feb. 1997, Part 3, Aug. 1997, pp. 1-159.

Fieldbus Standard For Use in Industrial Control Systems Part 4: Data Link Protocol Specification, ISA-S50. Feb. 1997, Part 4, Aug. 1997, pp. 1-148.

"Fieldbus Support For Process Analysis" by, Blevins et al., Fisher-Rosemount Systems, Inc., 1995, pp. 121-128.

"Fieldbus Technical Overview Understanding FOUNDATION™ fieldbus technology", Fisher-Rosemount, 1998, pp. 1-23.

"Hypertext Transfer Protocol—HTTP/1.0" by, Berners-Lee et al., MIT/LCS, May 1996, pp. 1-54.

"Infranets, Intranets, and the Internet" by, Pradip Madan, Echelon Corp, Sensors, Mar. 1997, pp. 46-50.

"Internet Technology Adoption into Automation" by, Fondl et al., Automation Business, pp. 1-5.

"Internet Protocol Darpa Internet Program Protocol Specification" by, Information Sciences Institute, University of Southern California, RFC 791, Sep. 1981, pp. 1-43.

"Introduction to Emit", emWare, Inc., 1997, pp. 1-22.

"Introduction to the Internet Protocols" by, Charles L. Hedrick, Computer Science Facilities Group, Rutgers University, Oct. 3, 1988, pp. 1-97.

"Is There A Future For Ethernet in Industrial Control?", Miclot et al., Plant Engineering, Oct. 1988, pp. 44-46, 48, 50.

LFM/SIMA Internet Remote Diagnostics Research Project Summary Report, Stanford University, Jan. 23, 1997, pp. 1-6.

"Managing Devices with the Web" by, Howard et al., Byte, Sep. 1997, pp. 45-64.

"Modular Microkernel Links GUI And Browser For Embedded Web Devices" by, Tom Williams, pp. 1-2.

"PC Software Gets Its Edge From Windows, Components, and the Internet", Wayne Labs, I&CS, Mar. 1997, pp. 23-32.

Proceedings Sensor Expo, Aneheim, California, Produced by Expocon Management Associates, Inc., Apr. 1996, pp. 9-21.

Proceedings Sensor Expo, Boston, Massachuttes, Produced by Expocon Management Associates, Inc., May 1997, pp. 1-416.

"Smart Sensor Network of the Future" by, Jay Warrior, Sensors, Mar. 1997, pp. 40-45.

"The Embedded Web Site" by, John R. Hines, IEEE Spectrum, Sep. 1996, p. 23.

"Transmission Control Protocol: Darpa Internet Program Protocol Specification" Information Sciences Institute, Sep. 1981, pp. 1-69.

"On-Line Statistical Process Control for a Glass Tank Ingredient Scale," by R.A. Weisman, *IFAC real Time Programming*, 1985, pp. 29-38.

"The Performance of Control Charts for Monitoring Process Variation," by C. Lowry et al., *Commun. Statis.—Simula.*, 1995, pp. 409-437.

"A Knowledge-Based Approach for Detection and Diagnosis of Out-Of-Control Events in Manufacturing Processes," by P. Love et al., *IEEE*, 1989, pp. 736-741.

"Advanced Engine Diagnostics Using Universal Process Modeling", by P. O'Sullivan, *Presented at the 1996 SAE Conference on Future Transportation Technology*, pp. 1-9.

Parallel, Fault-Tolerant Control and Diagnostics System for Feedwater Regulation in PWRS, by E. Eryurek et al., *Proceedings of the American Power Conference.*

"Programmable Hardware Architectures for Sensor Validation", by M.P. Henry et al., *Control Eng. Practice*, vol. 4, No. 10., pp. 1339-1354, (1996).

"Sensor Validation for Power Plants Using Adaptive Backpropagation Neural Network," *IEEE Transactions on Nuclear Science*, vol. 37, No. 2, by E. Eryurek et al. Apr. 1990, pp. 1040-1047.

"Signal Processing, Data Handling and Communications: The Case for Measurement Validation", by M.P. Henry, *Department of Engineering Science, Oxford University.*

"Smart Temperature Measurement in the '90s", by T. Kerlin et al., *C&I*, (1990).

"Software-Based Fault-Tolerant Control Design for Improved Power Plant Operation," *IEEE/IFAC Joint Symposium on Computer-Aided Control System Design*, Mar. 7-9, 1994 pp. 585-590.

A Standard Interface for Self-Validating Sensors, by M.P. Henry et al., *Report No. QUEL 1884/91*, (1991).

"Taking Full Advantage of Smart Transmitter Technology Now," by G. Orrison, *Control Engineering*, vol. 42, No. 1, Jan. 1995.

"Using Artifical Neural Networks to Identify Nuclear Power Plant States," by Israel E. Alguindigue et al., pp. 1-4.

"Application of Neural Computing Paradigms for Signal Validation," by B.R. Upadhyaya et al., *Department of Nuclear Engineering*, pp. 1-18.

"Application of Neural Networks for Sensor Validation and Plant Monitoring," by B. Upadhyaya et al., *Nuclear Technology*, vol. 97, No. 2, Feb. 1992 pp. 170-176.

"Automated Generation of Nonlinear System Characterization for Sensor Failure Detection," by B.R. Upadhyaya et al., *ISA*, 1989 pp. 269-274.

"In Situ Calibration of Nuclear Plant Platinum Resistance Thermometers Using Johnson Noise Methods," *EPRI*, Jun. 1983.

"Johnson Noise Thermometer for High Radiation and High-Temperature Environments," by L. Oakes et al., *Fifth Symposium on Space Nuclear Power Systems*, Jan. 1988, pp. 2-23.

"Development of a Resistance Thermometer For Use Up to 1600° C", by M.J. de Groot et al., *CAL LAB*, Jul./Aug. 1996, pp. 38-41.

"Survey, Applications, And Prospects of Johnson Noise Thermometry," by T. Blalock et al., *Electrical Engineering Department*, 1981 pp. 2-11.

"Noise Thermometry for Industrial and Metrological Applications at KFA Julich," by H. Brixy et al., *7th International Symposium on Temperature*, 1992.

"Johnson Noise Power Thermometer and its Application in Process Temperature Measurement," by T.V. Blalock et al., *American Institute of Physics* 1982, pp. 1249-1259.

"Field-based Architecture is Based on Open Systems, Improves Plant Performance", by P. Cleveland, *I&CS*, Aug. 1996, pp. 73-74.

"Tuned-Circuit Dual-Mode Johnson Noise Thermometers," by R.L. Shepard et al., Apr. 1992.

"Tuned-Circuit Johnson Noise Thermometry," by Michael Roberts et al., $7^{th}$ *Symposium on Space Nuclear Power Systems*, Jan. 1990.

"Smart Field Devices Provide New Process Data, Increase System Flexibility," by Mark Boland, *I&CS*, Nov. 1994, pp. 45-51.

"Wavelet Analysis of Vibration, Part I: Theory[1]," by D.E. Newland, *Journal of Vibration and Acoustics*, vol. 116, Oct. 1994, pp. 409-416.

"Wavelet Analysis of Vibration, Part 2: Wavelet Maps," by D.E. Newland, *Journal of Vibration and Acoustics*, vol. 116, Oct. 1994, pp. 417-425.

"Development of a Long-Life, High-Reliability Remotely Operated Johnson Noise Thermometer," by R.L. Shepard et al., *ISA*, 1991, pp. 77-84.

"Application of Johnson Noise Thermometry to Space Nuclear Reactors," by M.J. Roberts et al., *Presented at the 6th Symposium on Space Nuclear Power Systems*, Jan. 9-12, 1989.

"A Decade of Progress in High Temperature Johnson Noise Thermometry," by T.V. Blalock et al., *American Institute of Physics*, 1982 pp. 1219-1223.

"Sensor and Device Diagnostics for Predictive and Proactive Maintenance", by B. Boynton, *A Paper Presented at the Electric Power*

*Research Institute—Fossil Plant Maintenance Conference* in Baltimore, Maryland, Jul. 29-Aug. 1, 1996, pp. 50-1-50-6.

"Detection of Hot Spots in Thin Metal Films Using an Ultra Sensitive Dual Channel Noise Measurement System," by G.H. Massiha et al., *Energy and Information Technologies in the Southeast*, vol. 3 of 3, Apr. 1989, pp. 1310-1314.

"Detecting Blockage in Process Connections of Differential Pressure Transmitters", by E. Taya et al., *SICE*, 1995, pp. 1605-1608.

"Development and Application of Neural Network Algorithms For Process Diagnostics," by B.R. Upadhyaya et al., *Proceedings of the 29th Conference on Decision and Control*, 1990, pp. 3277-3282.

"A Fault-Tolerant Interface for Self-Validating Sensors", by M.P. Henry, *Colloquium*, pp. 3/1-3/2 (Nov. 1990).

"Fuzzy Logic and Artificial Neural Networks for Nuclear Power Plant Applications," by R.C. Berkan et al., *Proceedings of the American Power Conference*.

"Fuzzy Logic and Neural Network Applications to Fault Diagnosis", by P. Frank et al., *International Journal of Approximate Reasoning*, (1997), pp. 68-88.

"Keynote Paper: Hardware Complication-A New Technique for Rapid Prototyping of Digital Systems-Applied to Sensor Validation", by M.P. Henry, *Control Eng. Practice*, vol. 3, No. 7., pp. 907-924, (1995).

"The Implications of Digital Communications on Sensor Validation", by M. Henry et al., *Report No. QUEL 1912/92*, (1992).

"In-Situ Response Time Testing of Thermocouples", *ISA*, by H.M. Hashemian et al., Paper No. 89-0056, pp. 587-593, (1989).

"An Integrated Architecture For Signal Validation in Power Plants," by B.R. Upadhyaya et al., *Third IEEE International Symposium on Intelligent Control*, Aug. 24-26, 1988, pp. 1-6.

"Integration of Multiple Signal Validation Modules for Sensor Monitoring," by B. Upadhyaya et al., *Department of Nuclear Engineering*, Jul. 8, 1990, pp. 1-6.

"Intelligent Behaviour for Self-Validating Sensors", by M.P. Henry, *Advances In Measurement*, pp. 1-7, (May 1990).

"Measurement of the Temperature Fluctuation in a Resistor Generating 1/F Fluctuation," by S. Hashiguchi, *Japanese Journal of Applied Physics*, vol. 22, No. 5, Part 2, May 1983, pp. L284-L286.

"Check of Semiconductor Thermal Resistance Elements by the Method of Noise Thermometry", by A. B. Kisilevskii et al., *Measurement Techniques*, vol. 25, No. 3, Mar. 1982, New York, USA, pp. 244-246.

"Neural Networks for Sensor Validation and Plant Monitoring," by B. Upadhyaya, *International Fast Reactor Safety Meeting*, Aug. 12-16, 1990, pp. 2-10.

"Neural Networks for Sensor Validation and Plantwide Monitoring," by E. Eryurek, 1992.

"A New Method of Johnson Noise Thermometry", by C.J. Borkowski et al., *Rev. Sci. Instrum.*, vol. 45, No. 2, (Feb. 1974) pp. 151-162.

"Thermocouple Continuity Checker," IBM Technical Disclosure Bulletin, vol. 20, No. 5, pp. 1954 (Oct. 1977).

"A Self-Validating Thermocouple," Janice C-Y et al., IEEE Transactions on Control Systems Technology, vol. 5, No. 2, pp. 239-253 (Mar. 1997).

*Instrument Engineers' Handbook*, Chapter IV entitled "Temperature Measurements," by T.J. Claggett, pp. 266-333 (1982).

"emWare's Releases EMIT 3.0, Allowing Manufacturers to Internet and Network Enable Devices Royalty Free," 3 pages, PR Newswire (Nov. 4, 1998).

Warrior, J., "The IEEE P1451.1 Object Model Network Independent Interfaces for Sensors and Actuators," pp. 1-14, Rosemount Inc. (1997).

Warrior, J., "The Collision Between the Web and Plant Floor Automation," 6th. WWW Conference Workshop on Embedded Web Technology, Santa Clara, CA (Apr. 7, 1997).

Microsoft Press Computer Dictionary, 3rd Edition, p. 124.

"Internal Statistical Quality Control for Quality Monitoring Instruments", by P. Girling et al., *ISA*, 15 pgs., 1999.

Web Pages from www.triant.com (3 pgs.).

"Statistical Process Control (Practice Guide Series Book)", *Instrument Society of America*, 1995, pp. 1-58 and 169-204.

"Time-Frequency Analysis of Transient Pressure Signals for a Mechanical Heart Valve Cavitation Study," *ASAIO Journal*, by Alex A. Yu et al., vol. 44, No. 5, pp. M475-M479, (Sep.-Oct. 1998).

"Transient Pressure Signals in Mechanical Heart Valve Caviation," by Z.J. Wu et al., pp. M555-M561 (undated).

"Caviation in Pumps, Pipes and Valves," *Process Engineering*, by Dr. Ronald Young, pp. 47 and 49 (Jan. 1990).

"Quantification of Heart Valve Cavitation Based on High Fidelity Pressure Measurements," *Advances in Bioengineering 1994*, by Laura A. Garrison et al., BED- vol. 28, pp. 297-298 (Nov. 6-11, 1994).

"Monitoring and Diagnosis of Cavitation in Pumps and Valves Using the Wigner Distribution," *Hydroaccoustic Facilities, Instrumentation, and Experimental Techniques*, NCA-vol. 10, pp. 31-36 (1991).

"Developing Predictive Models for Cavitation Erosion," *Codes and Standards in A Global Environment*, PVP-vol. 259, pp. 189-192 (1993).

"Self-Diagnosing Intelligent Motors: A Key Enabler for Next Generation Manufacturing System," by Fred M. Discenzo et al., pp. 3/1-3/4 (1999).

"A Microcomputer-Based Instrument for Applications in Platinum Resistance Thermometry," by H. Rosemary Taylor and Hector A. Navarro, Journal of Physics E. Scientific Instrument, vol. 16, No. 11, pp. 1100-1104 (1983).

"Experience in Using Estelle for the Specification and Verification of a Fieldbus Protocol: FIP," by Barretto et al., Computer Networking, pp. 295-304 (1990).

"Computer Simulation of H1 Field Bus Transmission," by Utsumi et al., Advances in Instrumentation and Control, vol. 46, Part 2, pp. 1815-1827 (1991).

"Progress in Fieldbus Developments for Measuring and Control Application," by A. Schwaier, Sensor and Acuators, pp. 115-119 (1991).

"Ein Emulationssystem zur Leistungsanalyse von Feldbussystemen, Teil 1," by R. Hoyer, pp. 335-336 (1991).

"Simulatore Integrato: Controllo su bus di campo," by Barabino et al., Automazione e Strumentazione, pp. 85-91 (Oct. 1993).

"Ein Modulares, verteiltes Diagnose-Expertensystem für die Fehlerdiagnose in lokalen Netzen," by Jürgen M. Schröder, pp. 557-565 (1990).

"Fault Diagnosis of Fieldbus Systems," by Jürgen Quade, pp. 577-581 (Oct. 1992).

"Ziele und Anwendungen von Feldbussystemen," by T. Pfeifer et al., pp. 549-557 (Oct. 1987).

"PROFIBUS Infrastructure Measures," by Tilo Pfeifer et al., pp. 416-419 (Aug. 1991).

"Simulation the Time Behaviour of Fieldbus Systems," by O. Schnelle, pp. 440-442 (1991).

"Modélisation et simulation d'un bus de terrain: FIP," by Song et al, pp. 5-9 (undated).

"Field Bus Networks for Automation Systems Containing Intelligent Functional Unites," by W. Kriesel et al., pp. 486-489 (1987).

"Field Buses for Process Interconnection with Digital Control Systems," Tecnologia, pp. 141-147 (1990).

"Decentralised Systems with Real-Time Field Bus," Netzwerke, Jg. Nr. 3 v. 14.3, 4 pages (1990).

"Process Measurement and Analysis," by Liptak et al., Instrument Engineers' Handbook, Third Edition, pp. 528-530, (1995).

"Improving Dynamic Performance of Temperature Sensors With Fuzzy Control Techniques," by Wang Lei et al., pp. 872-873 (1992).

"Microsoft Press Computer Dictionary" 2nd Edition, 1994, Microsoft Press. p. 156.

International Search Report from Application No. PCT/US01/40791 with international filing date of May 22, 2001.

International Search Report from Application No. PCT/US01/40782 with international filing date of May 22, 2001.

International Search Report from Application No. PCT/02/14560 with international filing date of May 8, 2002.

International Search Report from Application No. PCT/US02/14934 with international filing date of May 8, 2002.

"On-Line Tool Condition Monitoring System With Wavelet Fuzzy Neural Network," by Li Xiaoli et al., pp. 271-276 (1997).

"Optimal Design of the Coils of An Electromagnetic Flow Meter," by Michalski, A. et al., IEEE Transactions on Magnetics, vol. 34, Issue 5, Part 1, pp. 2563-2566 (1998).

"Magnetic Fluid Flow Meter for Gases," Popa, N.C., IEEE Transactions on Magnetics, vol. 30, Issue 2, Part 1-2, pp. 936-938 (1993).

"New Approach to A Main Error Estimation for Primary Transducer of Electromagnetic Flow Meter," by Michalski, A., IEEE Instrumentation and Measurement Technology Conference Proceedings, vol. 2, pp. 1093-1097 (1998).

"Additional Information From Flowmeters Via Signal Analysis," by Amadi-Echendu, J.E. et al., IEEE Instrumentation and Measurement Technology Conference Record, vol. 7, pp. 187-193 (1990).

International Search Report from Application No. PCT/US02/06606 with international filing date of Mar. 5, 2002.

International Search Report from Application No. PCT/US02/30465 with international filing date of Sep. 25, 2002.

"Statistics Glossary: Time Series Data", by Easton et al., http://www.stats.gla.ac.uk/steps/glossary/time_series.html, Sep. 1997.

"The Indicators Story", Sustainable Seattle, pp. 55-59, 1998.

"Detecting Regimes in Temperature Time Series", by Clemins et al., *Artificial Neural Networks in Engineering, Proceedings*, pp. 727-732, 2001.

"Re: Digital Filter-Moving Average", The Math Forumn, http://mathforumn.org/discuss/sci.math/a/t/177212, Sep. 28, 1998.

U.S. Appl. No. 10/675,014, filed Sep. 2003, Longsdorf et al.

U.S. Appl. No. 10/744,809, filed Dec. 2003, Brown et al.

Annex to Form PCT/ISA/206 Communication Resulting to the Results of the Partial International Search, PCT/US2004/022736.

"Notification of Transmittal of The International Search Report or the Declaration", PCT/US2004/025291.

"Invitation to Pay Additional Fees and Annex to Form PCT/ISA/206".

"Notification of Transmittal of The International Search Report and the Written Opinion of the International Searching Authority, or the Declaration", PCT/US2004/022736.

Search Report and Written Opinion of the foreign application No. PCT/US2006/036415 filed Sep. 19, 2006.

"Notification of Transmittal of The International Search Report or the Declaration", PCT/US2004/017300.

U.S. Appl. No. 09/257,896, filed Feb. 25, 1999, Eryurek et al.

U.S. Appl. No. 09/409,098, filed Sep. 30, 1999, Eryurek et al.

U.S. Appl. No. 09/799,824, filed Mar. 5, 2001, Rome et al.

U.S. Appl. No. 09/855,179, filed May 14, 2001, Eryurek et al.

U.S. Appl. No. 09/852,102, filed May 9, 2001, Eryurek et al.

U.S. Appl. No. 09/972,078, filed Oct. 5, 2001, Eryurek et al.

U.S. Appl. No. 10/635,944, filed Aug. 7, 2003, Huisenga et al.

\* cited by examiner

PROCESS DIAGNOSTICS

CROSS-REFERENCE TO RELATED APPLICATION(S)

This application claims priority from U.S. Provisional Application Ser. No. 60/488,613 filed on Jul. 18, 2003 and entitled "PROCESS DIAGNOSTICS."

BACKGROUND OF THE INVENTION

The present invention relates to diagnostics for use in industrial processes, and in some embodiments particularly, to systems and methods for detecting fouling and corrosion in an industrial process.

Corrosion and fouling have been a longstanding concern in many industries. In the process industry, corrosion and fouling cause wall thinning and reduction of flow area, both of which are detrimental to the performance of pipes, conduits, cylinders, tanks, pressure vessels and the like. Additionally, corrosion and fouling may cause fixed equipment attached to the system to break down and fail. Depending on the system, such failures can be very costly.

Various techniques have been adopted to try to detect corrosion and/or fouling prior to equipment failure. One technique involves attaching a specialized corrosion and/or fouling detection device to the outside of the process structure, directing an ultrasonic signal transverse to the direction of flow through the wall of the structure, and detecting the reflected ultrasonic signal to measure changes in wall thickness over time, which may be indicative of plugging or fouling. Another technique involves directing an ultrasonic signal into a wall of a fluid-filled container. The ultrasonic signal propagates from a transmitting transducer to a receiving transducer. Analysis of the received waves determines the presence of corrosion on the inner wall. A third technique involves introducing an acoustic device into the fluid flow, which can be either fixed in place or floating like debris in the fluid, from which an acoustic signature of the pipe wall can be derived.

Additionally, a number of externally mounted detection devices have been proposed for detecting noise signature changes in fixed equipment. It is known in the art that as process fluid flows through any of the various types of fixed equipment (boilers, mixers, heat exchangers, valves, and the like), a process noise signature is produced. As plugging, fouling or corrosion occurs, the process noise signature changes.

Unfortunately, conventional fouling and corrosion detection devices and techniques require specialized detection equipment, which are separate from existing monitoring and control equipment. Such equipment can be expensive to add to an existing monitoring and control system. There remains an on-going need in the art for a system and method for detecting fouling and/or corrosion of fixed equipment that does not require specialized equipment. Embodiments of the present invention provide solutions to these and other problems, and offer other advantages over the prior art.

SUMMARY OF THE INVENTION

A diagnostic device for use in a industrial process includes monitoring electronics or diagnostic circuitry configured to diagnose or identify a condition or other occurrence in the industrial process. The system can be implemented in a process device such as a flowmeter, and in one example an acoustic flowmeter. A transducer can also be used and a frequency response, such as resonant frequency, can be observed. A method is also provided.

DETAILED DESCRIPTION OF THE PREFERRED EMBODIMENTS

In general, flowmeters are known in the art, which utilize acoustic sensors to detect spontaneous vortex creation and propagation in a fluid flowing within a pipe. Acoustic sensors positioned along the exterior pipe wall identify and track such vortices based on acoustic patterns generated by the vortices, and the flow through the pipe can be calculated based on those patterns. Conventionally, such acoustic detection systems require a turbulent flow having a velocity of at least three feet per second.

It is also known in the art that devices in an industrial processes tend to generate process noise. Typically, field devices are designed to isolate sensors from the process noise or to filter out the process noise in order to extract a desired measurement from the measured acoustic data. The present invention makes use of the background or process noise to monitor the health of fixed equipment or process devices (such as turbines, pumps, rotors, mixers, and other rotating or reciprocating equipment, heat exchangers, valves, thermowells, piping, and the like). In general, as such devices become fouled or corroded, their noise contribution changes. More importantly, when a process device begins to fail, subtle changes may be detected in the process noise associated with the failing device. Such process noise changes may begin at frequency ranges well above or well below the audible range of human hearing, but are nevertheless acoustically detectable.

In one aspect, the present invention utilizes typically filtered background noise to monitor processes for acoustic or pressure variations, which may be indicative of fouling and corrosion of the system. Where acoustic flowmeters have associated circuitry which includes a microprocessor, a firmware upgrade which includes algorithms for processing background noise may be sufficient to adapt an existing acoustic flowmeter to monitor fouling and corrosion. In new acoustic flowmeter systems, circuitry and/or software is provided to monitor and detect changes in background noise which may be indicative of fouling and corrosion.

Figure 1:
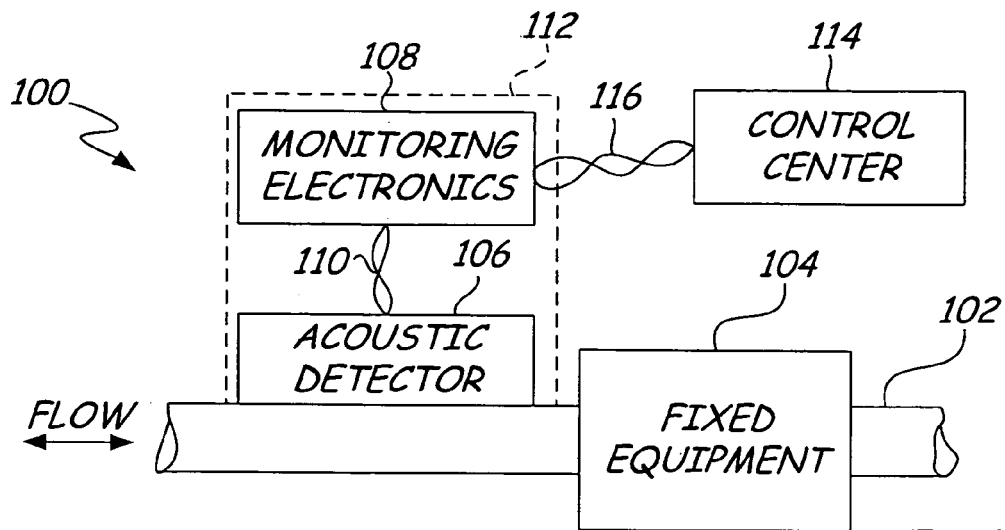
FIG. 1 is a simplified block diagram of an acoustic flowmeter with fouling and corrosion detection functionality for detecting fouling of fixed equipment within an industrial process according to an embodiment of the present invention.

FIG. 1 is a simplified block diagram of a process diagnostic system 100 according to an embodiment of the present invention. The diagnostic system 100 includes a pipe 102 with fixed equipment 104 coupled to the pipe 102. Fluid flow within the pipe 102 is measured using an acoustic flowmeter 112, which detects acoustic patterns generated by vortices within the fluid flow using an acoustic detector 106, which typically includes three or more acoustic sensors. As used herein, the term "acoustic" refers to a repeating or non-repeating pressure signal or fluctuation, which may or may not occur at a frequency within an audible range, but which is nevertheless detectable.

The acoustic detector 106 is coupled to monitoring electronics 108 via leads 110. The monitoring electronics 108 are coupled to control center 114 via communications link 116 (which may be wired or wireless link). In general, the communications link 116 may be standard cabling, such as standard two, three, or four wire loops for carrying standard field device communications via a communications standard such as HART, FIELDBUS, or any other communication standard. In some embodiments, the diagnostic system is completely powered with power received over a process control loop such as link 16.

In general, the walls of the pipe 102 cause the formation of vortices within the fluid flowing in the pipe 102. Acoustic detector 106 coupled to the exterior of the pipe 102 detects acoustic patterns generated by the vortices. Flow through the pipe 102 can be calculated from the detected acoustic patterns. During the process of identifying and tracking vortices, the acoustic detector 106 monitors acoustic signals within the flow. In general, the process noise is carried through both the physical process structures and the fluid flow. Rather than discarding information unrelated to the vortices, the present invention processes the non-vortex related information against a baseline signature. The degree to which the measured information differs from the baseline is utilized in the present invention to predict fouling and/or corrosion of process equipment.

In general, the diagnostic function is accomplished by determining the acoustic noise signature produced by process fluid flowing through fixed equipment which is operating normally. This acoustic noise signature can be stored and used as a baseline signature. Deviations from the baseline can be used to predict an extent of fouling and/or corrosion of the fixed equipment.

The acoustic flowmeter 100 is attached to the piping 102 adjacent to fixed equipment 104. The acoustic sensors of the flowmeter 100 are used to sense both acoustic patterns generated by vortices in the process flow and the acoustic noise signature generated by the process fluid flowing through the fixed equipment 104.

At installation, or at other times determined by the user, this acoustic noise signature is sampled and stored as a reference. During operation, a plugged or fouled condition of the target device or piping can be detected by noting changes in the process noise. If a change in process noise meets or exceeds a predetermined threshold, an alarm or warning can be placed on the output signal.

The process noise signature can be established using any number of signal processing or statistical algorithms. In one embodiment, a Fast Fourier Transform (FFT) is used to establish the noise signature from measured acoustic signals.

In one embodiment, the electronics are co-located in a single package. These electronics input and condition the acoustic sensor signal, as well as identify individual vortices based on their acoustic patterns. In addition, the electronics provide the capability of storing set-up values in non-volatile memory. At a minimum, the electronics 108 includes a digital processing capability.

In one embodiment, the monitoring electronics 108 includes a microprocessor adapted to condition acoustic sensor signals including extracting signals from a high noise environment, calibrating and setting up the sensor and associated monitoring functions, and generating output signals. In addition, the monitoring electronics 108 includes a digital computation capability with appropriate software adapted to transform noise signal measurements via an FFT algorithm, and comparator functionality for comparing the noise signature produced by the FFT algorithm to a reference noise signature (baseline signature). In an alternative embodiment, these functions are handled by individual circuitry or software algorithms.

In one embodiment, the acoustic flowmeter 100 is positioned upstream from the fixed equipment. In this embodiment, the acoustic flowmeter 100 senses a reflected noise signature. If the signature amplitude and/or frequency profile change more than a predetermined amount for a given flow rate as measured by the flowmeter 100, an alarm or warning can be placed on the flowmeter output signal to alert the control center 114.

The monitoring electronics 108 includes input functionality for setting initial values via an external device or via a local, integral operator interface. In a preferred embodiment, the monitoring electronics 108 support bi-directional communication via a digital bus, such as HART, Foundation Field Bus, CAN, or other digital media. In another embodiment, the monitoring electronics 108 supports bi-directional communications via a wireless protocol, such as wireless standard 802.11(b), infrared signaling, simple text messaging via cellular or wireless links, and the like. This communication capability can be utilized to set initial values and to output various levels of alarm criticality. In addition, acoustic sensor health can be reported via the communication capability. For this type of meter, electronics are typically not 4-20 mA loop powered. However, loop power may be feasible if the meter is operated in burst mode.

One example of a type of fixed equipment that can be monitored according to embodiments of the present invention is rotary fixed equipment. It is known in the art that the acoustic signature of rotating equipment changes shortly before full failure occurs. For example, bearings that are about to fail due to fatiguing of the races emit a characteristic squealing sound, which varies greatly from the normal process signature. One example of rotary fixed equipment is a pump and its attached motor which rotate, thereby emitting a characteristic noise signature. This typical noise signature is sensed by the acoustic sensors integral to the flowmeter 100, and recorded by the flowmeter 100 as a reference noise signature during calibration, commissioning, or on operator request. If problems develop with the rotary equipment bearings, or if for example, a pump vane breaks, the noise signature will change markedly. By periodically monitoring the background noise signature (such as by a request from a control center 112 or via a local operator interface, such as a keypad and display on the transmitter housing), the acoustic flowmeter 100 can detect the change in the noise signature, process the noise signals through an algorithm (such as a Fast Fourier Transform), compare the processed noise signal with a stored signature, and generate an alarm if they differ by more than a predetermined amount. By comparing the signatures after the Fast Fourier Transform has been applied, new frequency bands of high amplitude can be readily identified.

In a catalyst cracker (sometimes referred to as a "cat cracker"), an acoustic flowmeter 100 coupled to a pipe segment 102, which is coupled to a light fractions port on the cat cracker structure can be used to measure light fraction flow and to monitor the health of the cat cracker. When a change in the noise pattern or a brief, high amplitude noise event occurs (such as when a piece of ceramic breaks away from the cat cracker structure), an alarm can be placed on the output signal of the acoustic flowmeter. A plugged or fouled condition of the cat cracker can be detected as a decrease in noise amplitude that exceeds a predetermined variation from the reference.

Thus, the present invention provides advantages over prior art acoustic flowmeters, by extending the capability of the flowmeter to detect or predict fouling or plugging in fixed equipment or piping. The flowmeter 100 is simple to use and requires no additional devices or wiring beyond the basic flowmeter. Moreover, the flowmeter 100 can monitor both the target device and associated piping for plugging and fouling (or corrosion).

Figure 2:
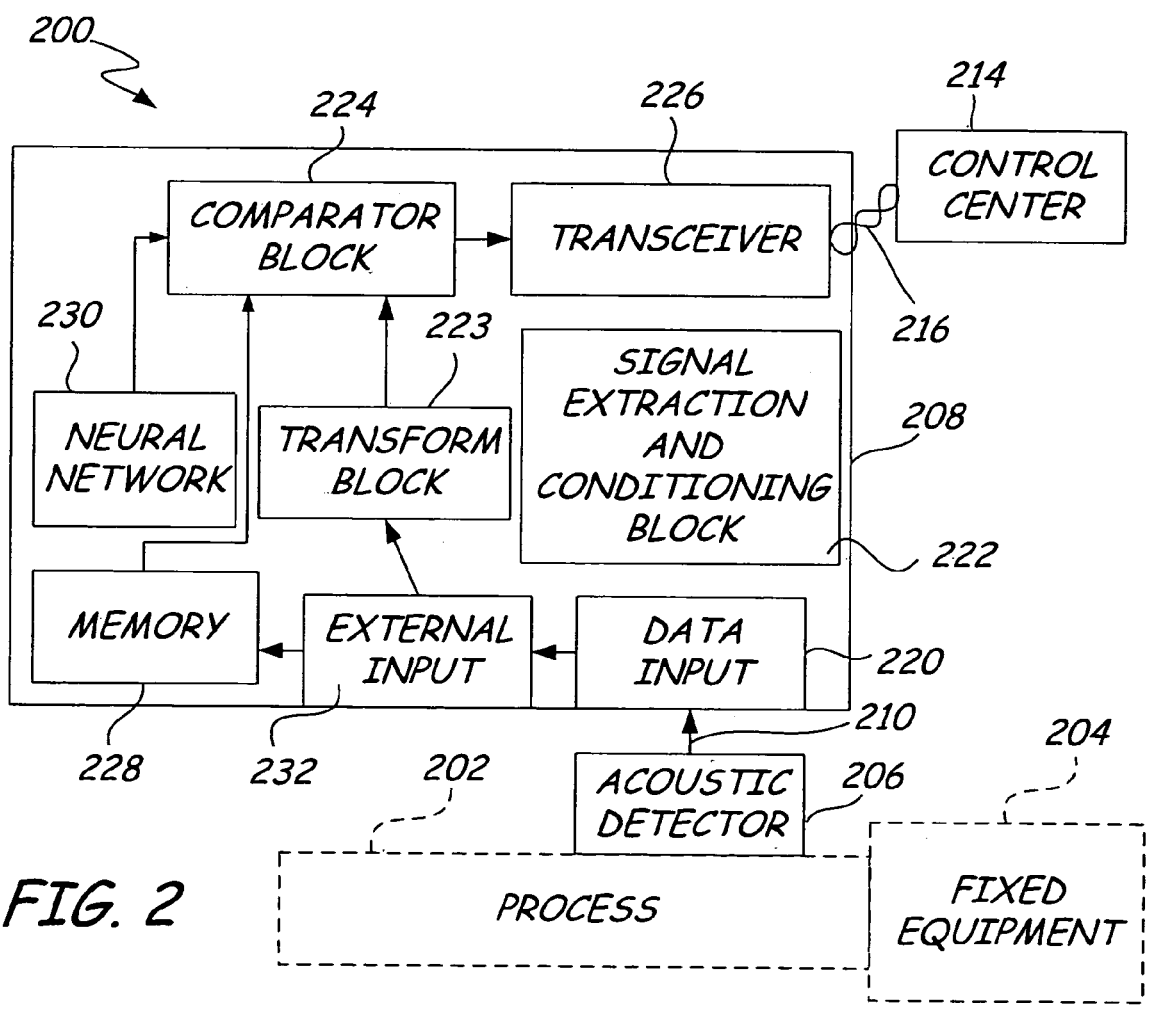
FIG. 2 is a simplified block diagram of the monitoring electronics of the acoustic flowmeter of FIG. 1.

FIG. 2 illustrates an expanded block diagram of process diagnostic system 200 according to an embodiment of the present invention. The diagnostic system 200 includes a pipe segment 202 and fixed equipment 204 coupled to the pipe segment 202. An acoustic detector 206 (which may be comprised of a plurality of acoustic sensors) is coupled to an external wall of the pipe segment 202 and within acoustic range of fixed equipment 204. In general, the range within which an acoustic detector 206 can monitor noise generated by a device, such as fixed equipment 204, varies depending on the acoustic conductivity of the process fluid, the sensitivity of the sensors within the acoustic detector 206, and the extent of the process noise. Thus, the detector 206 is positioned relative to the fixed equipment 204 in sufficiently close proximity that the detector 206 receives acoustically detectable noise signals caused by the fixed equipment 204.

The acoustic detector 206 is coupled to monitoring electronics 208, which may or may not be contained within the same housing as the acoustic detector. The acoustic detector 206 and the monitoring electronics 208 are coupled via leads 210.

Generally, the acoustic detector 206 monitors noise patterns generated by vortices within the fluid flow, as well as process-related noise through the wall of the pipe segment 202. Measurement information is passed via leads 210 to a data input 220 of the monitoring electronics 208 and written to input buffer 221. The signal extraction and grooming block 222 retrieves the measurement information from the buffer 221, and extracts flow information from the measurement information. The signal extraction and grooming block 222 then generates an output signal indicative of the flow. The output signal is passed to transceiver 226 for transmission to control center 214 via communications link 216.

The measurement information is read from the buffer 221 by a transform block 223, which processes the measurement information according to an algorithm. In a preferred embodiment, the algorithm is a Fast Fourier Transform. The transform block 223 processes the measurement information into an acoustic signature representative of the process noise. The acoustic signature is passed to a comparator block 224, which compares the acoustic signature with a reference signature from memory 228, which was initialized during setup. In one embodiment, a neural network 230 interacts with the comparator 224 to correlate the measured information with baseline data stored in the memory 228. In this manner, acoustic changes in background noise or in noise associated with a specific device can be isolated. The magnitude of the change is an indication of the extent of fouling and/or corrosion of the system or of a specific device.

Thus, an acoustic flowmeter can be adapted to provide process monitoring and diagnostics, in addition to flow measurements, without requiring a unique fouling/corrosion detector system. In other words, field devices that include acoustic sensors can be adapted to perform two functions (flow measurement and process diagnostics), without requiring large scale changes. In one embodiment, the neural network 230 and the memory 228 may be provided by the control center 214, thereby allowing the microprocessor 224 to isolate the flow vortex measurements from background noise and to return both portions of the signal to the control center 214 for processing against the baseline signal to determine whether fouling and/or corrosion has occurred in the system. This makes it possible to make a software adjustment in the circuitry of the monitoring electronics, without changing the circuit arrangement.

It should be understood by a worker skilled in the art that the systems of FIGS. 1 and 2 passively monitor process noise generated by the fluid flow. Additionally, it should be understood that fixed equipment (104/204) refers to physical elements of the system 100/200 which are fixed in place (as opposed to portable sensors and the like) Fixed equipment 104/204 may include pumps, catalystic crackers, mixers, valves, heat exchangers, boilers, or any other device attached to industrial process. The fixed equipment may also refer to vessels, conduits, piping, and tanks, or any other structure associated with the process.

Figure 3A:
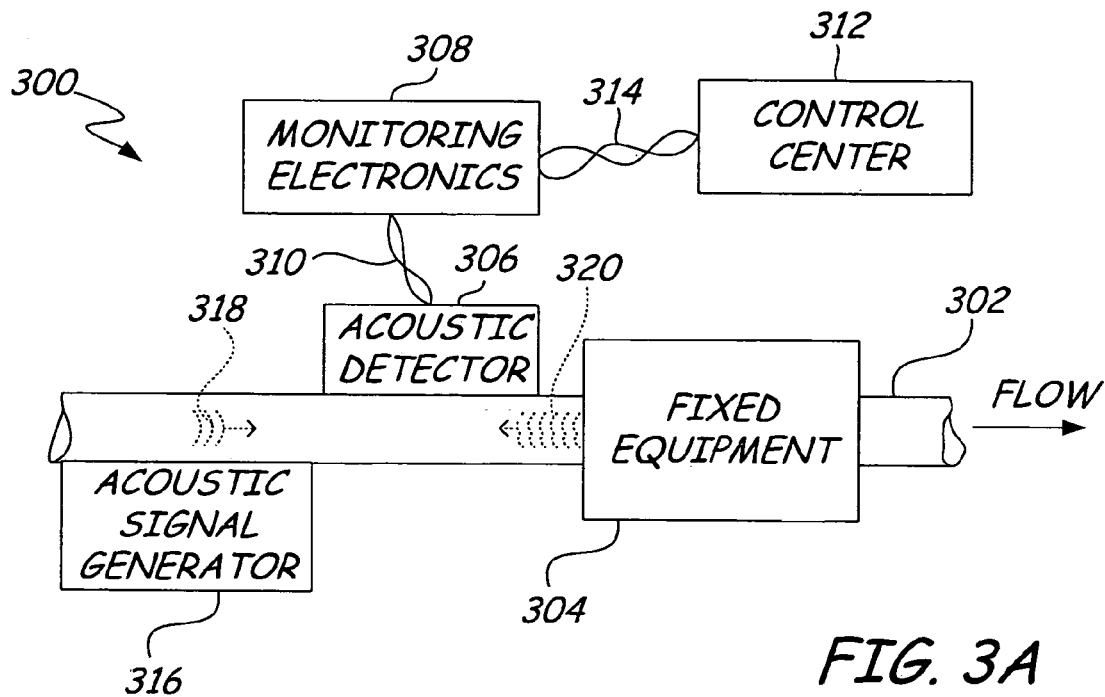
FIGS. 3A and 3B illustrate simplified block diagrams of fouling and corrosion detectors having an acoustic signal generator according to an embodiment of the present invention.
Figure 3B:
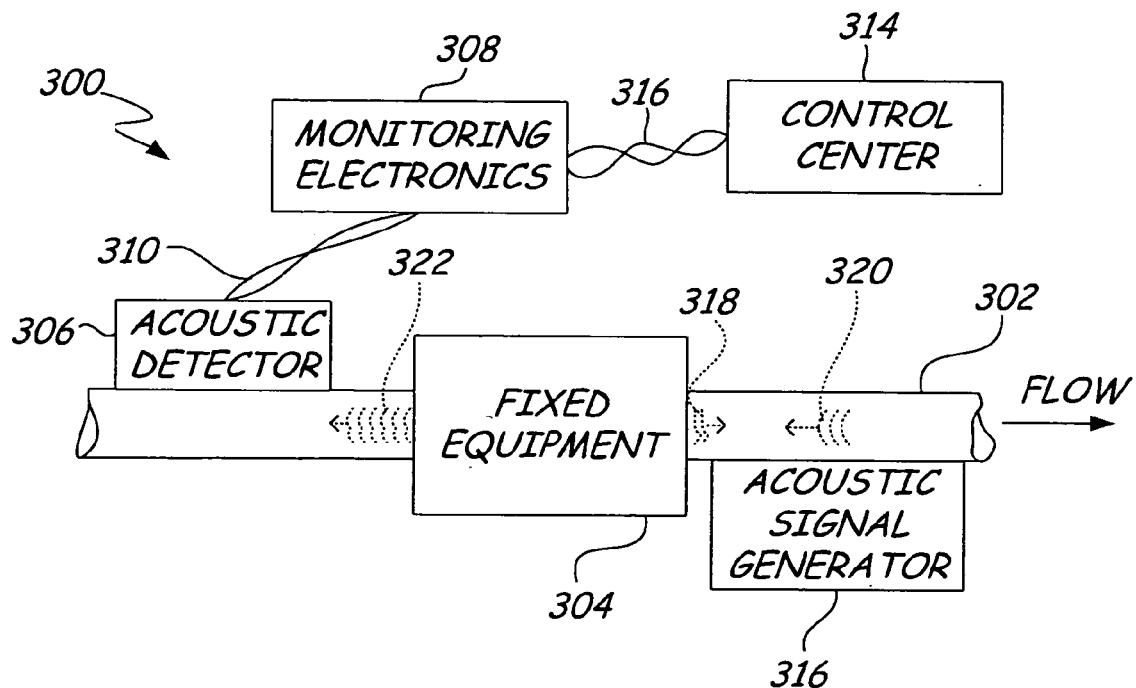

FIGS. 3A and 3B illustrate simplified block diagrams of a process diagnostic system 300 having an active corrosion/fouling detection system. The system 300 includes a pipe segment 302 containing a process fluid. Fixed equipment 304 (such as a catalystic cracker, mixer and the like) is coupled to the pipe segment 302. An acoustic detector 306 is coupled to the pipe segment 302 near the fixed equipment 304, for measuring a flow of process fluid within the pipe segment 302. The acoustic detector 306 is coupled to monitoring electronics 308 via leads 310. The monitoring electronics 308 send and receive information to and from control center 312 via communications link 314, which may be wired or wireless.

A mechanical 'pinging' device or acoustic impulse generator 316 (hereinafter referred to as "acoustic generator 316") is coupled to the pipe segment 302 and adapted to generate an acoustic signal 318. The pipe segment 302 is pinged or otherwise excited, and acoustic sensors of the acoustic detector 306 measure a frequency response of the pipe segment 302. Build up and corrosion along the pipe wall can be detected based on the detected change in resonant frequency.

Digital processing functionality of the monitoring electronics 308 is used to determine the resonant frequency and damping of the pipe section. During the initial meter installation, a reference resonant frequency and damping value is established and stored by exciting the pipe section and measuring the frequency response. The present measured value of the resonant frequency and damping can be compared with the initial values. If the initial values change by more than a predetermined amount, the acoustic flowmeter 300 generates an alarm signal indicative of possible fouling and/or corrosion of the pipe section.

In addition to an acoustic impulse generator 316, the acoustic generator 316 may be a piezoelectric transducer element. In such an embodiment, the resonant frequency can be obtained by driving the acoustic transducer over a frequency range of interest. Again, by using the acoustic sensors of the acoustic detector 306 to measure the frequency response, it is possible to determine a resonant frequency and damping of the meter section.

It should be noted that the acoustic generator 316 need not be permanently fixed to the pipe section 302, such that adjacent pipe sections can be tested simply by moving the acoustic generator 316 to the adjacent pipe section. For a critical region of pipe sections, several acoustic generators or transducers can be mounted such that each critical section of piping has an acoustic generator or transducer affixed to it. The acoustic flow meter 300 can be configured to excite each generator 316 at a unique time, and determine the resonant frequency and damping of the piping section associated with that generator 316. If the resonant frequency deviates by more than a predetermined amount, the acoustic flowmeter 300 generates an alarm or warning of possible corrosion or erosion damage in that pipe section 302.

In a preferred embodiment, the flowmeter 300 includes an acoustic detector having three or more acoustic sensors adapted to listen for acoustic patterns generated by vortices spawned within the fluid flow. The flow is measured based on the time it takes for a spawned vortex to pass the sensors.

In an alternative embodiment, the acoustic generator 316 transmits an acoustic signal into the fluid flow toward the fixed equipment 304. A reflected signal 320 representative of the wetted surfaces of the fixed equipment 304 is reflected back from the fixed equipment. The acoustic detector 306 can detect both the transmitted acoustic signal 318 and the reflected signal 320. Alternatively, the detector 306 can measure only the reflected signal 320. In either case, the monitoring electronics 308 processes the detected signal(s) to determine variations from a baseline measurement. The extent of the variation is then indicative of fouling and/or corrosion of the fixed equipment 304.

In FIG. 3A, the acoustic signal generator 316 is positioned upstream from the fixed equipment 304 and from the acoustic detector 306. The acoustic signal generator 316 may be located downstream of the detector 306 or even within the same housing. In a preferred embodiment, the signal generator 316 is positioned as shown, so as to allow the detector 306 to measure the frequency and phase of the transmitted signal 318, as well as the frequency and phase shift of the reflected portion of the signal (or of the resonant frequency of the equipment).

In FIG. 3B, the acoustic signal generator 316 (or excitation device) is positioned on an opposite side of the fixed equipment 304 from the acoustic detector 306. The acoustic signal generator 316 transmits an acoustic signal 318 through the fixed equipment 304 or excites the system into resonance. The acoustic detector 306 either detects the transmitted signal or measures the resonant frequency of the system (as previously discussed). The transmitted signal 318 is partially reflected (as indicated by acoustic waves 320, and is partially transmitted through the fixed equipment 304. The transmitted signal 322 travels through the process fluid within the pipe 302 toward the acoustic detector 306, which is adapted to measure fluid flow within the pipe 302, and also to detect the transmitted signal 322, which passes through the fixed equipment 304.

As previously indicated, the transmitted signal 322 is measured by the acoustic detector 306 and compared by the monitoring electronics 308 to a stored acoustic signature. In an alternative embodiment, the raw measurement data is transmitted to the control center 312, where the data is processed and compared to stored baseline information.

In general, in an original installed state, the fixed equipment 304 can be modeled as two transfer functions: a reflection transfer function and a transmission transfer function. Each transfer function is unique to the particular device, and the detected reflected or transmitted waveform is a characteristic signature of the device. Subsequently measured waveforms may vary from the characteristic signature (in phase, amplitude, frequency, and so on) such that the measured reflection/transmission reflects variations in the fixed equipment 304, which may be attributed to fouling or corrosion. Thus, the detected acoustic signature may provide a basis for predicting corrosion or fouling conditions in the system 300.

The system for creating and detecting a change in the subject pipe sections' resonant frequencies can consist of a means to excite the pipe into resonance for a very short period of time. Pressure and/or acoustic devices capable of detecting changes in resonant frequency can be used to detect fouling based on such a change. In a preferred embodiment, the "listening" device is a pressure sensor or an acoustic flowmeter. The pinging or acoustic signal generator is a piezoelectric driven mechanical oscillator that can be used to excite the pipe into resonance, or a "hammer" type device for delivering a mild impulse to the pipe. These devices can be based on magnetic solenoid technology or a piezoelectric driver used in pulsed mode. The resonance checks can include time, frequency, or code multiplexed so as to allow multiple sections to be evaluated by a single meter. Either the meter's primary or auxiliary electronics can be utilized to perform the diagnostic functions.

Conventionally, acoustic flowmeters provided reasonably accurate flow measurements at rates at or above 3 feet per second. This limitation is largely due to the fact that vortices generated at the lower flow velocities are of lower energy. This makes their characteristic audio signal harder to separate from background process noise.

Figure 4A:
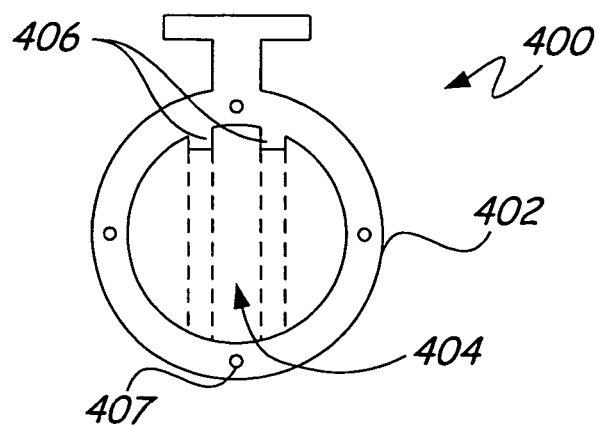
FIG. 4A is a simplified front-view of a vortex shedding plate for facilitating acoustic measurement of low flow processes according to an embodiment of the present invention.

FIG. 4A illustrates a front-view of a shedding plate 400 for inducing vortices in the process fluid according to an embodiment of the present invention. The shedding plate 400 preferably has a ring-shaped body 402 defining an opening 404. Two obstructions 406 are disposed within the opening 404 to cause vortex creation in a fluid flow. Fastener openings 407 may be provided in the body 402 to provide fastening means for securing the plate 400 in a process. The two obstructions 406 may be partial obstructions. In a second embodiment, the two obstructions 406 may extend across the entire opening (as shown in phantom). In a third embodiment, only one obstruction is provided. By inserting a shedding plate 400 into the fluid flow upstream from the acoustic detector, the acoustic detector may remain functional at low flow rates, such as below 1 foot per second.

Figure 4B:
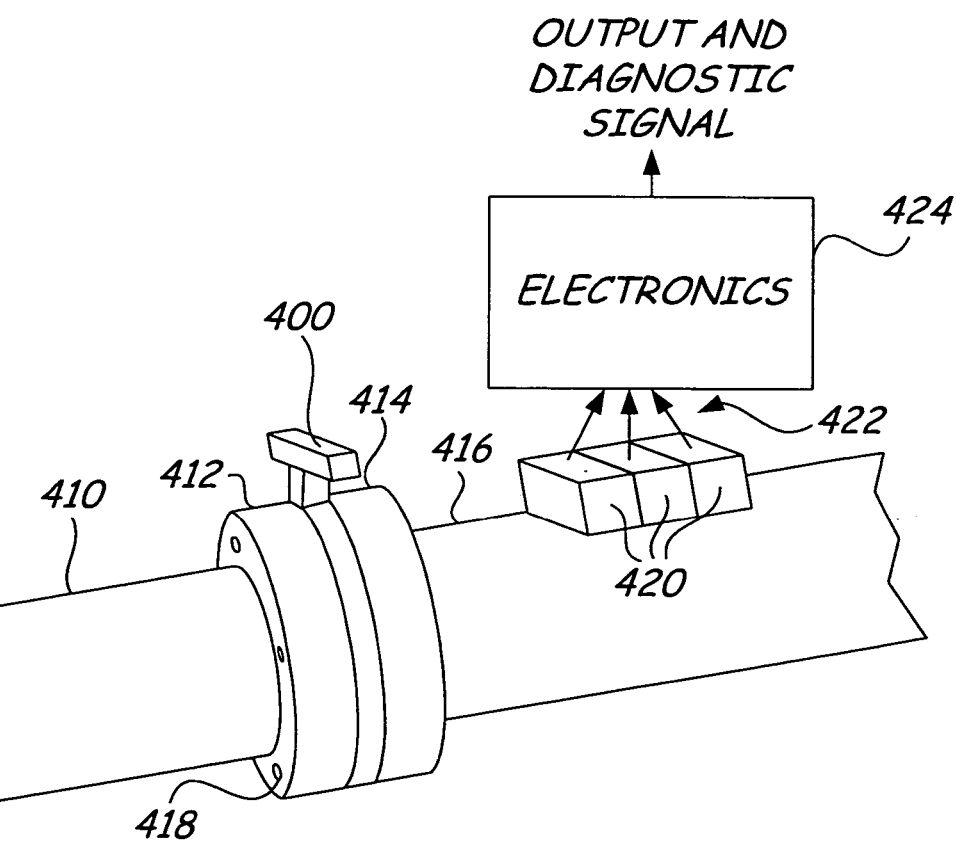
FIG. 4B is a simplified perspective view of a corrosion and fouling detection system including the vortex shedding plate of FIG. 4A according to an embodiment of the present invention.

FIG. 4B shows a simplified perspective view of an acoustic detector assembly 408 having a shedding plate 400 sandwiched between flange elements 412 and 414, which are coupled to pipe sections 410 and 416, respectively. Fasteners 418 secure the shedding plate 400 and flange elements 412 and 414. Acoustic detector 422, which is comprised of three acoustic sensors 420 arranged in line with the direction of flow, is disposed on an outside surface of pipe section 416. The acoustic detector 420 is coupled to electronics 424, which is adapted to produce an output signal that is indicative of flow and a diagnostic signal indicative of the health of the system adjacent to the detector 422.

In this embodiment, the rate of flow is detected based on the travel time of a detected vortex as the vortex as it flows past each of the sensors. The time differential and the known distance between the sensors 420 provides a reliable basis from which to calculate a flow rate, which is accurate even at flow rates below 3 feet per second. By introducing small teeth or other small, vortex generating geometries upstream of the audio sensors inside the pipe section used for measurement, it is possible to create vortices with much stronger characteristic audio signals. This allows the acoustic flowmeter technology to be extended to lower flow rates down to near one foot per second.

Figure 5A:
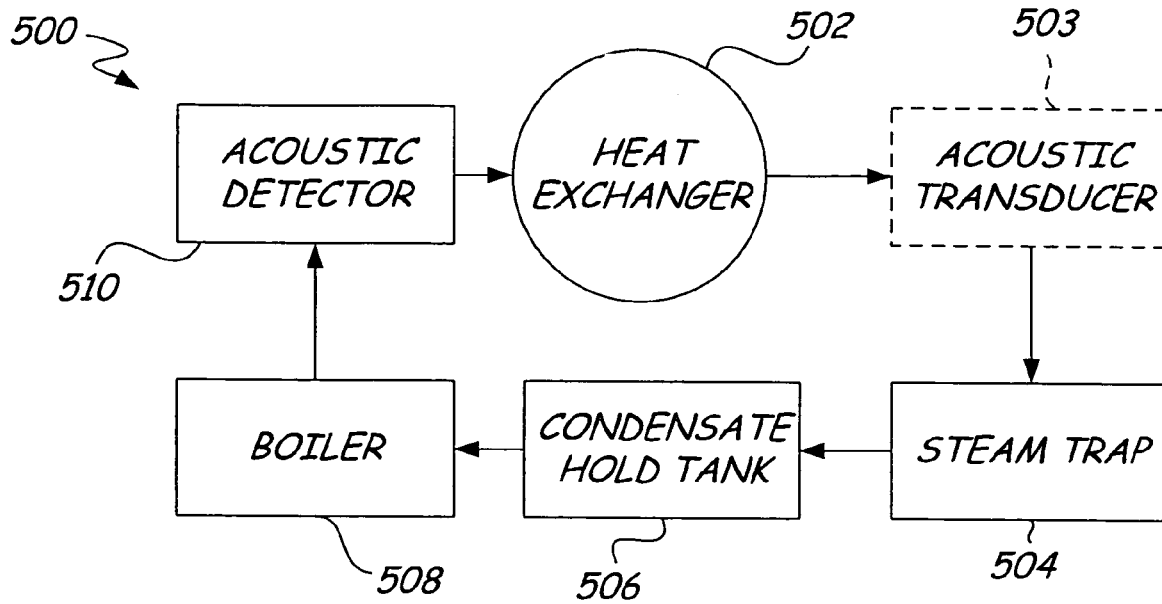
FIGS. 5A and 5B illustrate variations of the corrosion and fouling detector in a process including a heat exchanger according to an embodiment of the present invention.
Figure 5B:
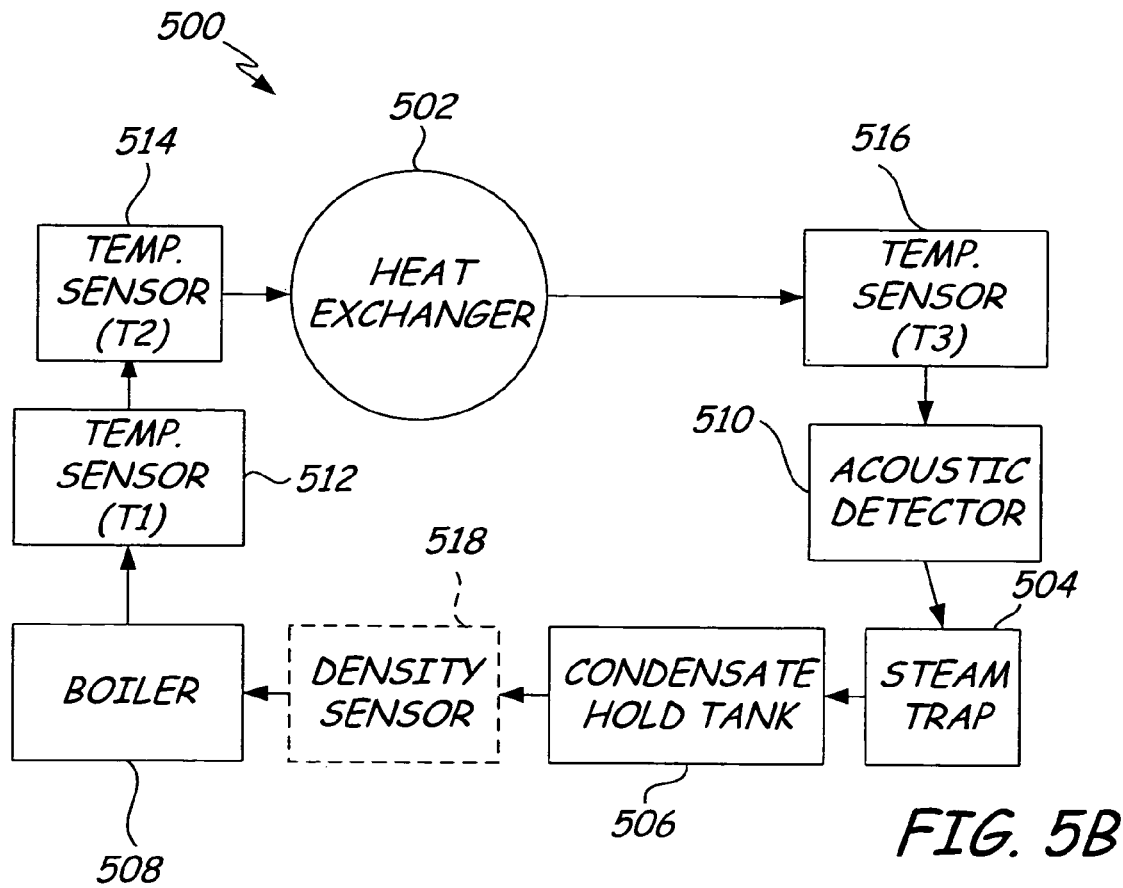

FIGS. 5A and 5B illustrate two embodiments of a heat exchanger system 500. In FIG. 5A, the heat exchanger system 500 includes a heat exchanger 502, which is coupled to a steam trap 504 on one end, and a boiler 508 on the other end. A condensate holding tank 506 is coupled between the steam trap 504 and the boiler 508. Finally, an acoustic detector 510 is coupled to the flow outlet end of the heat exchanger 502.

In general, the boiler 508 heats liquid in the system 500 to high temperature steam, which travels through the piping and into the heat exchanger 502. The heat exchanger 502 exchanges heat with an adjacent process (not shown), causing the steam to cool in the exchanger. The cooled steam condenses into liquid form in a steam trap, flows past the acoustic detector 510, and flows into the condensate holding tank 506, from which it is pumped back into the boiler 508 for reheating. It should be understood that the system 500 is simplified. A number of elements common to industrial heat exchanger systems have been omitted for the sake of clarity, such as valves to waste and for automatic or manual blowdown, as well as for introduction of "makeup" water.

Both the boiler 508 and the heat exchanger 502 contribute process noise to the flow. The boiler 508 heats the water using burners, which may contribute noise to the process. The steam itself, as it flows through the pipes, may contribute noise, and the heat exchanger 502, where the steam enters the exchanger 502, contributes a reflected noise signature. These acoustic signals can be detected by the acoustic detector 510 to determine a characteristic noise signature of the system. Typically, the exchanger 502 is the most likely element to experience fouling and/or corrosion, and therefore will most often be the device on which the acoustic detector 510 is focused; however, the acoustic detector 510 is capable of monitoring more than one device.

An acoustic transducer 503 (shown in phantom) may be introduced between the heat exchanger 502 and downstream elements to establish an active fouling and corrosion detector. In a preferred embodiment, the acoustic transducer 503 is coupled to the exchanger wall such that the transducer is in close proximity to the process fluid. The transducer 503 may have coatings and/or isolation materials between it and the process fluid for protection from corrosion. The electronics in the acoustic detector 510 generates a signal containing one or more frequencies to drive the transducer 503. Returned signals to the transducer 503 can be detected to estimate process fluid properties, as well as the overall health of the sending transducer 503. The acoustic detector 510 listens for the generated acoustic signal. This signal contains both fluid property information and fouling/plugging information. The electronics of the acoustic detector 510 remove the process fluid property information from the detected signal, leaving only fouling/plugging information, which is then evaluated by reducing it to an equivalent acoustic impedance through the exchanger. If the acoustic impedance increases beyond a threshold value, the acoustic detector 510 will generate an alarm signal to the control-center (shown in FIGS. 1-3B).

In this embodiment, the acoustic detector 510 includes electronics adapted to determine flow velocity, to drive the acoustic transducer 503 (which may be piezoelectric transducer), to evaluate returned signals, and to communicate an alarm condition when plugging or fouling is detected.

This type of active (transducer driven) fouling and corrosion detection system can also evaluate the process fluid for major property changes. For some process, for example, an occasional anomaly occurs where a slug of debris or a layer of higher solids content is temporarily present in the process fluid. This anomaly, if allowed to persist, can lead to rapid exchanger fouling. The reference acoustic signature can be used to detect major events of this nature and to provide the user (or control center) with an alarm specific to the detected event.

This type of device can be fabricated such that groups of tubes in the exchanger 502 each include a sending transducer 503. In a preferred embodiment, these transducers are oriented such that most of the acoustic energy is directed through the target tube group. Each tube group is evaluated during a different time slice. Since fouling/plugging occurs slowly (over hours at least), these time slices can be up to a few seconds without loss of immediacy of the detection. By monitoring groups of tubs, detection of area-specific fouling/corrosion is readily accomplished.

It should be understood that the acoustic flowmeter with the acoustic detector 510 can determine the amplitude and frequency distribution of the noise signals. As the exchanger or reactor plugs, process noise originating at the acoustic transducer 503 at the other end of the exchanger from the acoustic detector 510 is attenuated. By detecting a degree of attenuation, the detector 510 can predict the extent of fouling or corrosion within the exchanger and associated piping. If plugging exceeds a preset limit, an alarm or warning is generated and sent to, for example, a control system.

To improve sensitivity, an additional upstream and downstream transducer can be employed. The flowmeter's acoustic detector 510 can utilize the transducer signals to determine more precisely the amount of process noise attenuation.

The transducer 503 can be provided with its own electronics, and can be self-diagnosed by the electronics. A portion of the transmitted signal will be reflected from structures within the system. The reflected signal can be used to monitor the strength of the transducer's acoustical output signal. As the transducer 503 ages, degrades, or breaks, this signal degrades or disappears. As this happens, the electronics associated with the transducer 503 can output a warning that it is failing. If multiple transducers 503 are used, each transducer 503 may include self-diagnostic electronics.

This embodiment provides a sensitive, predictive method of determining the extent of exchanger fouling as an optional diagnostic capability of an acoustic flowmeter 510. The invention allows for easy application and mounting and does not require multiple pressure/volume analysis to provide information on fouling and plugging. Maintenance on the transducers 503 and acoustic sensors of the acoustic detector 510 can be performed when the exchanger 502 is serviced. One particular advantage of this embodiment is that coating and fouling of the exchanger 502 is detected directly, rather than inferred from secondary pressure volume measurements. Moreover, for systems that utilize an acoustic transducer 503, process fluid properties can be estimated based on the signal attenuation. By utilizing existing acoustic flowmeter technology, the cost of implementing a diagnostic system in this manner is low, and is mainly related to small incremental hardware changes to the original flow meter, such as an additional board for noise processing.

FIG. 5B illustrates the exchanger system 500 with a temperature sensor 512 positioned between boiler 508 and acoustic detector 510. Additionally, temperature sensor 514 is positioned between the acoustic detector 510 and the exchanger 502, and a temperature sensor 516 is positioned between the exchanger and the condensate hold tank 506.

The temperature values can be monitored to determine the degree that plugging/fouling of the exchanger 502 has occurred. The three temperature sensors 512, 514, 516 provide a measurement of the change in process fluid temperature due to passing through the exchanger 502 (temp. sensors 514 and 516), as well as the inlet temperature of the thermal exchange media (temp. sensor 512). These temperature sensor signals, combined with the flow rate, are used to detect changes in exchanger efficiency, which can be attributed to coating, fouling or plugging. For a given set of values for flow and a given thermal exchange media inlet temperature, the temperature difference is measured across the exchanger (T2-T3) and from the boiler 508 to the inlet of the exchanger 514 (T1-T2). Initial values are stored in a non-volatile memory and are compared with subsequent values over time. If measured values show a temperature variation across the exchanger 502 that is substantially changed from the stored difference, plugging or fouling may be inferred and an alarm can be generated.

The heat transfer characteristics of a clean, properly operating exchanger provide a basis for estimating what the change in temperature drop should be for any given measured temperature in the system. Given consistent process fluid properties, the device can provide a warning or alarm if the measured values are significantly different from the expected values.

The acoustic detector 510 can also listen for acoustic signals, allowing for redundant checking for exchanger fouling/plugging using acoustic sensing. If process fluid properties vary widely for a particular installation, a fluid density sensor 518 may be included to correct for the effect of density changes on the expected temperature drop across the exchanger 502. In one embodiment, the acoustic flowmeter is adapted to directly determine the process fluid density, similar to a vortex meter. Alternatively, a pressure difference across the exchanger can be measured. This differential pressure, along with the temperature and flow through the exchanger, can be used to estimate the fluid density. For most liquids, the fluid properties have only small effects on the flow, as compared with plugging/fouling, so the fluid density can often be neglected. However, for gases, changes in fluid properties can produce significant changes in the temperature difference across the exchanger. These changes in fluid properties must be taken into account when testing for significant changes in exchanger performance as an indication of plugging/fouling.

Electronics associated with the acoustic detector 510 receive an acoustic detector signal 510, condition the flow sensor signal, as well as receiving and conditioning the temperature sensor signals. The electronics provide the capability of storing reference values in nonvolatile memory. At a minimum, the electronics includes digital processing capability, such that the presently sensed values of flow, the inlet temperature, and the temperature difference across the exchanger 504 can be compared with reference values. If degradation of exchanger performance exceeds a predetermined limit, an alarm or warning is generated that possible plugging/fouling may occur.

As a redundant measure, the diagnostic function can be verified by determining an acoustic noise signature of a properly operating exchanger from the process fluid flowing through the exchanger. The flowmeters acoustic sensors are used both to measure acoustic patterns generated by vortices in the fluid and to sense the acoustic noise signature produced by the process fluid as it flows through the exchanger. At installation, or at other times determined by a user, the flow noise is sampled and stored as a reference. During operation, a plugged or fouled condition of the exchanger or of related piping can be detected by noting a change in noise amplitude that exceeds a predetermined threshold.

The exchanger fouling detection system provides a sensitive, predictive means for determining the extent of exchanger fouling as an optional diagnostic capability of a flow meter. The flowmeter is simple and readily implemented, and diagnostics are achieved by monitoring temperature differences across the exchanger as a primary indication of fouling/corrosion. The flowmeter and sensors can be serviced when the exchanger is serviced. If multiple temperature sensors are used, multiple differential measurements may be taken, and the variations in the temperature measurements can be utilized to more precisely detect area fouling within the system. By using appropriate flowmeter technology or additional sensors, process fluid properties can be estimated. Moreover, wetted components can be standard sensors/transmitters, so that only the electronics associated with the flowmeter are unique.

Figure 6:
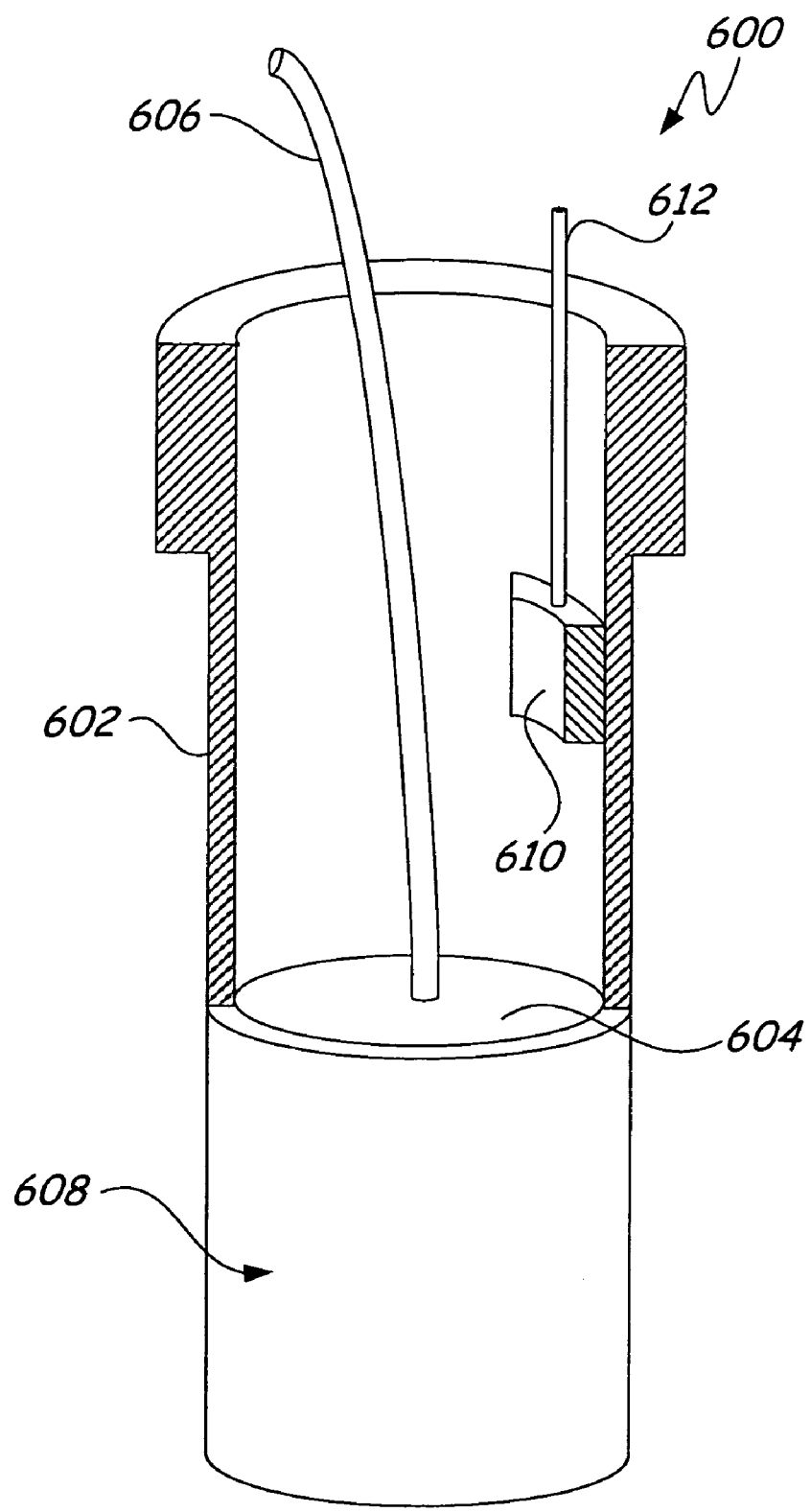
FIG. 6 is a simplified cross-sectional diagram of a thermowell fitted with a transducer for detecting fouling and corrosion on an external surface of the thermowell according to an embodiment of the present invention.

FIG. 6 is a simplified cross-sectional view of a thermowell 600 according to an embodiment of the present invention. Conventionally, a common failure mode for temperature sensors, and especially for thermowells, is coating or fouling of the outside surface of the thermowell or the sensor. This coating or fouling causes a change in the thermal time constant of the sensor, thereby "detuning" the control system. Badly coated temperature sensors can cause problems in monitoring applications, where temperate limits can be exceeded in the process, but the reporting of the out of range temperature is delayed by the increased time constant due to coating.

The thermowell 600 includes a means for detecting when coating or fouling has progressed to an unacceptable thickness. The thermowell 600 includes a cylindrical body 602 defining a chamber for securing a temperature sensor 604. A temperature sensor lead 606 extends from a transmitter (not shown) through the chamber and into the temperature sensor. Coating/fouling builds up on the outside surface 608 of the thermowell 602, causing the time constant to change.

To detect unacceptable build up or fouling, a piezoelectric transducer 610 is fixed inside the thermowell 600. In alternative embodiments, the transducer may be magnetic, electrostatic, or any other transducer type. The geometry of the thermowell 600 is configured so that the transducer 610 can excite the thermowell 600 into resonance. The excitation frequency of the transducer is varied by accompanying electronics until a maximum amplitude of the thermowell 600 displacement is determined and stored. If the thermowell 600 is coated or fouled, the coating adds mass to the thermowell 600, altering its resonant frequency. If this change in resonant frequency exceeds a predetermined limit, the transmitter coupled to the thermowell 600 sends an alarm or "caution" signal to the process operator in charge of this measurement point (or generally to a control center).

In corrosive process fluids that do not coat or foul the thermowell 600, the mass of the thermowell 600 will still change over time as the corrosive process fluid attacks the thermowell 600. As the corrosive process fluid pits or otherwise corrodes (erodes) the surface of the thermowell 600, the mass of the thermowell 600 decreases, thereby causing a change in the resonant frequency. The preset or predetermined limit may be a deviation (plus or minus) from a baseline.

Figure 7A:
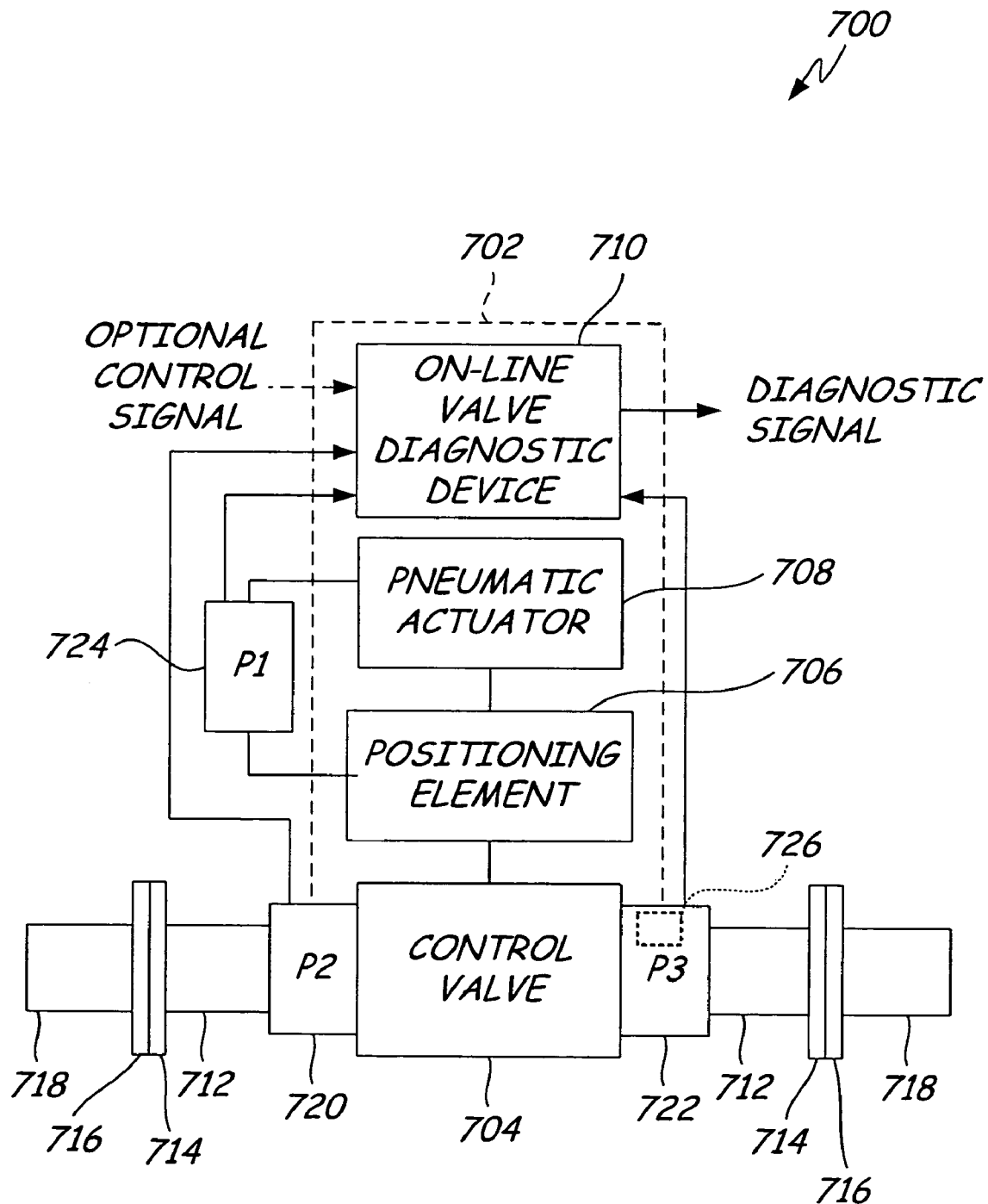
FIG. 7A is a simplified block diagram of a pneumatic valve with diagnostic functionality according to an embodiment of the present invention.

FIG. 7A illustrates a simplified block diagram of a pneumatic actuator valve 700 having a diagnostic function according to an embodiment of the present invention. A common failure mode that is responsible for loss of capacity in process plants is valve malfunction, such as if a valve sticks, if a valve is stuck, or if the stem has broken away from the plug (in a plug-type valve). Another failure mode involves cavitation of the valve for a period of time, such that the internal geometry of the valve is severely eroded. Cavitation is a problem associated with pressure changes across valves and pumps, wherein small gas bubbles form and then violently collapse as pressure and temperature conditions affecting the process fluid change as the process fluid passes through the device. The collapsing of the bubbles can cause severe erosion to the device, even over a short period of time. It is difficult to detect cavitation as it is occurring, except when frequencies associated with cavitation rise above twenty KiloHertz. Most cavitation can be detected by a worker skilled in the art by listening to the subject device or by audio sensors and specialized electronics adapted to detect a change. Pressure and/or acoustic sensors can be adapted to listen to the process and to detect the patterns associated with cavitation. The user can be notified if a cavitation event is detected. Insipient cavitation can be associated with changes in a device signature in the frequency range of greater than 20 kHz. By making pressure and/or acoustic sensors capable of measuring higher frequencies, incipient cavitation can be detected and reported. Cavitation of a valve may produce a sound similar to marbles hitting each other Additionally, the I/P or I/Positioner may also fail, causing what appears to be a valve malfunction.

The valve 700 includes a housing 702 containing a pneumatically actuated control valve 704, a positioning element 706, a pneumatic actuator 708, and an on-line valve diagnostic device 710. In general, the positioning element 706 (I/P or I/Positioner) positions the control valve 704. The actuator 708 controls the positioning element.

The pneumatic actuator valve 700 is mounted to a pipe segment 712 having flange elements 714 on each end, which mate with flange elements 716 on adjacent piping 718. The valve 700 includes three pressure sensors 720, 722, and 724. Pressure sensor 724 (corresponding to pressure P1) is adapted to measure a pneumatic actuator pressure. Pressure sensors 720 and 722 (corresponding to pressures P2 and P3, respectively) are positioned between the control valve 704 and the adjacent pipe sections 712. Generally, pressure sensors 720 and 722 are positioned in gaskets with pressure taps positioned on either side of the control valve 704.

By measuring the upstream pressure (P2), downstream pressure (P3) and pneumatic actuator pressure (P1), the diagnostic device 710 is able to provide a diagnostic output if the valve malfunctions. Specifically, the upstream pressure (P2) and the pressure across the valve (P2-P3) are monitored to determine the valve operating point. The pressure to the pneumatic actuator is also monitored. In a properly (normally) operating valve, if the actuation pressure (P1) is changed, the valve operating point (P2-P3) will also change. The actuator pressure (P1) may change as a result of the control loop changing due to a process disturbance or a need to run the process at a different operating point.

The downstream pressure sensor 722 can be selected to have a high bandwidth such that it can sense acoustic frequencies in the KiloHertz (KHz) range. Alternatively, a pressure sensor 722 with an additional acoustic sensor 726 (shown in phantom) are connected to a tap provided for the pressure sensor 722. This acoustic sensor 726 provides a high frequency capability, which can be used to predict/detect cavitation.

If the control signal to the valve 700 is made available to the diagnostic device 710, via Foundation Fieldbus, HART, or by wiring the control loop through the diagnostic device 710, the diagnostic device 710 can monitor the control signals for changes to cause a change in the actuation pressure. If no change in actuation occurs, the diagnostic device 710 can report a possible malfunction of the positioning element 706.

Figure 7B:
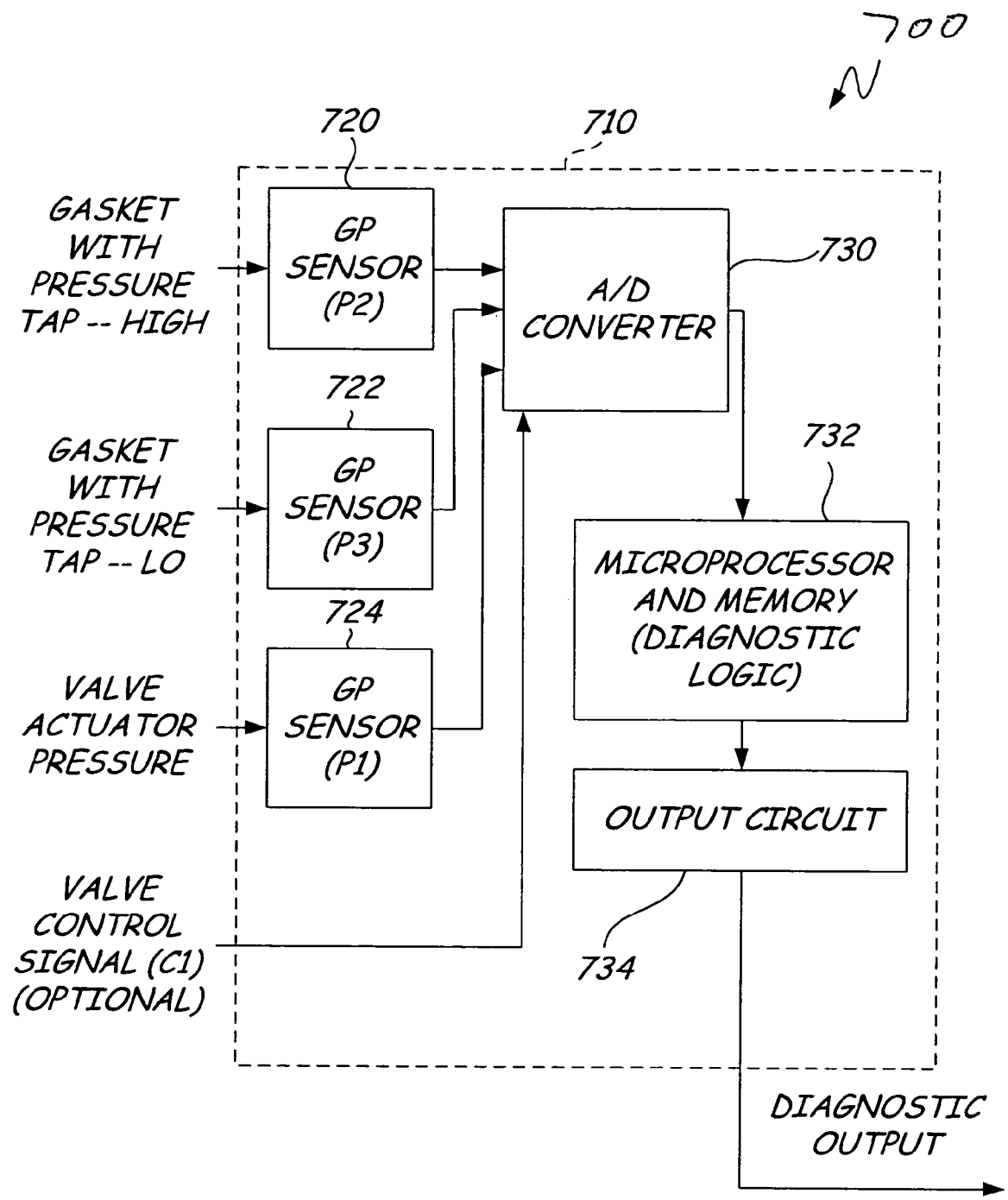
FIG. 7B is a simplified block diagram of the control circuitry for the pneumatic valve of FIG. 7A.

FIG. 7B is simplified expanded view of the on-line valve diagnostic device 710 of FIG. 7A. As shown, a gage pressure (GP) sensor (P2) 720 measures the process pressure via a pressure tap in a gasket provided upstream of the control valve 704. A GP sensor (P3) 722 measures the process pressure via a pressure tap in a gasket provided downstream of the control valve 704. A GP sensor (P1) 724 measures a valve actuator pressure. Each of the measured values for actuator pressure, upstream and downstream pressures are provided to the A/D converter 730, which converts the raw analog data to a digital output. The digital output is then delivered to the microprocessor and memory (diagnostic logic) circuitry 732, which processes the digital output into a signal indicative of the health of the valve. The signal is then provided to the output circuit 734, which transmits the diagnostic output.

Figure 7C:
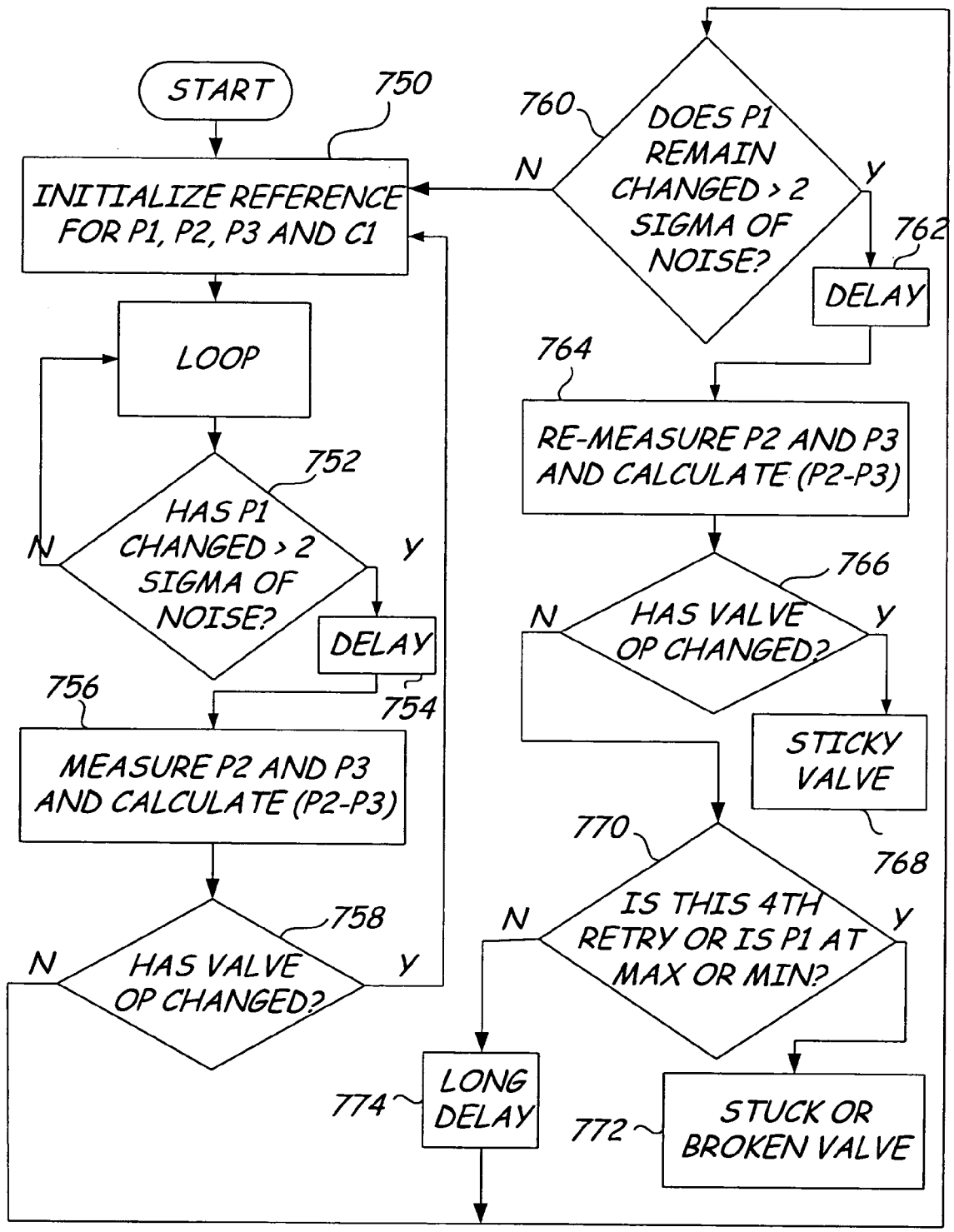
FIG. 7C is a simplified flow diagram of a process for detecting valve failure with the system of FIGS. 7A and 7B, according to an embodiment of the present invention.

FIG. 7C is a simplified flow diagram of the operation of the pneumatic actuator valve 700 according to the embodiment of FIGS. 7A and 7B. Upon startup, the diagnostic device initializes reference values for the actuator valve pressure (P1), the upstream pressure (P2), the downstream pressure (P3) and the valve control signal (C1) (block 750). Once the reference values are initialized, the device checks for a stuck or broken valve (blocks 752-774).

The device tests the actuator valve pressure (P1) to see if the value has changed by more than two sigma (block 752). If the value has not changed by more than two sigma, the device continues to retest the actuator valve pressure (P1) every couple of seconds until the value has changed. If the value has changed, the device waits a second or two to allow the pressure across the valve to stabilize (step 754). Then, the device measures the upstream and downstream pressures (P2 and P3, respectively), and calculates the pressure across the valve (P2-P3) (step 756). If the valve operational pressure changed (step 758), the device again initializes the reference values for the actuator valve pressure (P1), the upstream pressure (P2), the downstream pressure (P3) and the valve control signal (C1) (block 750). Once the reference values are initialized, the device checks for a stuck or broken valve (blocks 752-774).

If the valve operational pressure has not changed, the device tests the actuator pressure (P1) to see if it remains changed by more than two sigma (block 760). If not, the device re-initializes the reference values for the actuator valve pressure (P1), the upstream pressure (P2), the downstream pressure (P3) and the valve control signal (C1) (block 750). Once the reference values are initialized, the device checks for a stuck or broken valve (blocks 752-774).

If the actuator pressure (P1) remains changed by an amount greater than two sigma of noise (block 760), the device waits for the pressure across the valve to stabilize (block 762). The device re-measures the upstream and downstream, pressures (P2 and P3), and calculates the differential pressure (P2-P3) (block 764). The device tests to see if the valve operational pressure has changed (block 766). If the operational pressure has changed, then the pneumatic valve is probably sticking (block 768). If the valve operational-pressure has not changed (block 766), then the device checks if this is the fourth retry or if the actuator pressure (P1) is at a minimum or a maximum (block 770). If either condition is true, then the valve is probably stuck or broken (block 772). If the conditions are false, then the device waits for a period of time to allow the pressures to stabilize (in most instances a few seconds is sufficient) (block 774), and then retests the actuator pressure (P1) to see if it remains changed by an amount greater than two sigma of noise (step 760).

The embodiment of FIGS. 7A-7C provide an on-line method of determining if a valve is sticking, stuck or if its stem is broken, and provide an on-line method of predicting/determining if a valve is cavitating. Since the system involves three simple gasket plates with taps, the diagnostic valve system is simple to mount and requires no valve body modification or tapping (though tapping of the valve body is another possible embodiment). The set-up is straightforward, in part, because the diagnostic is based on a continuously updated valve operating point and the pneumatic actuation pressure. The device can be added onto existing systems, and can operate without access to DCS, Valve I/P, or positioner control data. Moreover, continuous operation is not required, thereby allowing low power consumption. A diagnostic check once every few seconds is more than sufficient to verify if a valve has malfunctioned. The device need not be powered by the control loop. Independent power supplies are possible, and communication can be via local, analog, HART, FFB, Ethernet, or any other digital bus. The diagnostic device 700 provides I/P and I/positioner malfunction checks if the set point information is available to the diagnostic device. Pressure sensors do not need to be high performance, but rather just highly reliable. Finally, the diagnostic system 700 can be utilized on all flanged valves from any manufacturer, and can be used on non-flanged valves if the valve body is tapped for pressure ports.

In general, the present invention takes advantage of changes in acoustic spectral content and amplitude, which is characteristic of problems in process flow equipment. Both acoustic flowmeters and pressure sensors can be adapted to detect this spectral content and amplitude. This makes it possible to provide exchanger plugging/fouling diagnostics using pressure and/or acoustic sensing capabilities, to provide cavitation detection diagnostics using pressure and/or acousting sensing capability, to provide acoustic flowmetering at low flow ranges below 3 feet per second, to evaluate fouling or plugging by actively exciting a pipe segment and testing its resonant frequency against a reference.

Figure 8:
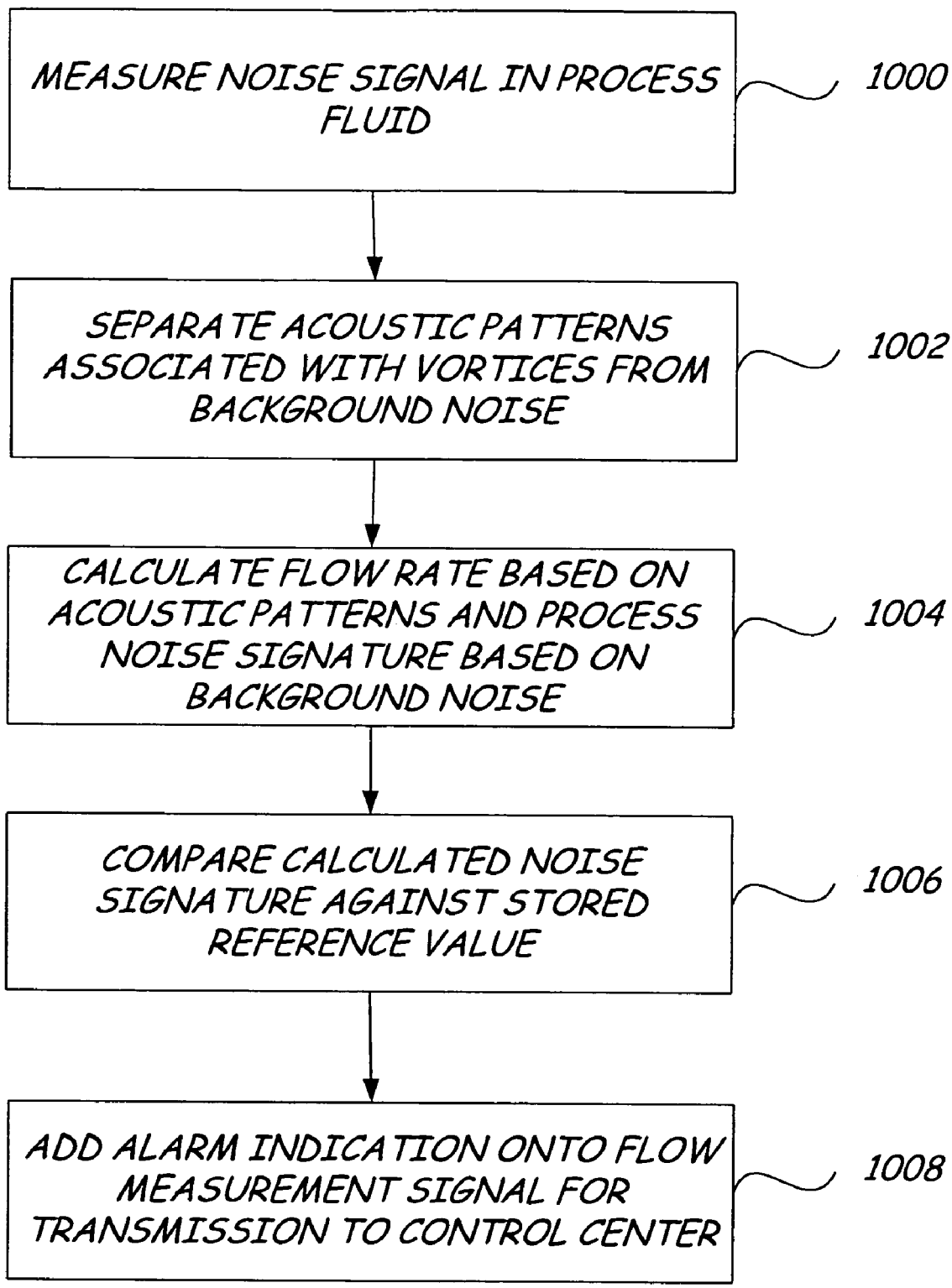
FIG. 8 is a simplified flow diagram of a process of performing process measurements and diagnostics in a single device according to an embodiment of the present invention.

FIG. 8 is a simplified flow diagram of a method for detecting fouling or corrosion in an industrial process according to an embodiment of the present invention. A noise signal is measured in the process fluid of an industrial process (block 1000). The diagnostic circuit separates acoustic patterns associated with vortices from background noise (block 1002). The diagnostic device calculates a flow rate based on the acoustic patterns and a process noise signature based on background (process) noise (block 1004). As previously discussed, the background noise signature is calculated using an algorithm such as a Fast Fourier Transform.

The calculated process noise signature is then compared with the stored reference value (block 1006), which corresponds to a process noise signature of the system in a known good state. An alarm signal or indication is added onto the flow measurement signal for transmission to a control center (block 1008), if the calculate noise signature deviates from the stored reference by more than a predetermined limit.

Although the present invention has been described with reference to preferred embodiments, workers skilled in the art will recognize that changes may be made in form and detail without departing from the spirit and scope of the invention.

What is claimed is:

1. A diagnostic device for detecting fouling and corrosion in process equipment comprising:
   at least one detector for measuring a frequency response coupled to the process equipment wherein the frequency response is related to fouling or corrosion of the process equipment;
   a transducer coupled to a process element and adapted to excite the process element into resonance; and
   a diagnostic circuit coupled to the at least one detector and the transducer, the diagnostic circuit adapted to trigger the process element into resonance via a command sent to the transducer and to process the measured frequency response from the at least one detector, the diagnostic circuit adapted to compare the measured frequency response to a stored reference frequency response and to produce a diagnostic signal indicative of health of the process equipment indicative of fouling or corrosion of the process equipment based on a deviation of the measured frequency response from the stored frequency response.

2. The diagnostic device of claim 1 wherein the diagnostic circuitry comprises:
   a transformation block adapted to transform the measured frequency response into a process signature; and
   a comparator adapted to compare the process signature to a stored reference signature to identify a change.

3. The diagnostic device of claim 1 wherein the transducer comprises:
   an acoustic generator coupled to the process equipment and adapted to generate an acoustic signal within the process equipment.

4. The diagnostic device of claim 3 wherein the acoustic generator is coupled to the diagnostic circuit, wherein the diagnostic circuit is adapted to initiate generation of an acoustic signal at a particular frequency by the acoustic generator.

5. The diagnostic device of claim 1 and further comprising:

fixed equipment coupled to a pipe section, the fixed equipment generating process noise as process fluid flows through the fixed equipment;

wherein the change is indicative of corrosion or fouling of the fixed equipment.

6. The diagnostic device of claim 1 and further comprising:

a non-volatile memory buffer adapted to store the stored frequency response, the stored frequency response comprising a transformed process noise signal of process fluid flowing through an industrial process when components of the industrial process are functioning properly.

7. The diagnostic device of claim 1 wherein the frequency response comprises:

a signal composed of a plurality of frequencies.

8. The diagnostic device of claim 1 wherein the diagnostic circuitry comprises:

a neural network.

9. The diagnostic device of claim 1 and further comprising:

an external input or local operator interface for configuring the diagnostic circuit.

10. The diagnostic device of claim 1 wherein the process equipment is configured to couple to a heat exchanger.

11. The diagnostic device of claim 1 including a temperature sensor.

12. The diagnostic device of claim 1 including a structure to introduce vortexes in a process fluid.

13. The diagnostic device of claim 1 wherein the deviation of the measured frequency response is indicative of a mass change of the process equipment.

14. The diagnostic device of claim 13 wherein the mass change is a loss of mass indicative of corrosion.

15. The diagnostic device of claim 13 wherein the mass change is a gain of mass indicative of build up.

16. The diagnostic device of claim 1 wherein the process equipment comprises:

a thermowell with a temperature sensor for measuring a process temperature of a process fluid.

17. The diagnostic device of claim 1 wherein the process equipment comprises:

a pipe section.

18. The diagnostic device of claim 1 wherein the process equipment comprises:

an obstruction extending into a fluid flow.

* * * * *